United States Patent [19]
Morris et al.

[11] Patent Number: 5,989,210
[45] Date of Patent: Nov. 23, 1999

[54] RHEOLYTIC THROMBECTOMY CATHETER AND METHOD OF USING SAME

[75] Inventors: John Edward Morris, Minneapolis; Cindy M. Setum, Plymouth; William J. Drasler, Minnetonka; Hieu V. Le, Minneapolis; Robert G. Dutcher, Maple Grove, all of Minn.

[73] Assignee: Possis Medical, Inc., Coon Rapids, Minn.

[21] Appl. No.: 09/019,728

[22] Filed: Feb. 6, 1998

[51] Int. Cl.⁶ .................................................. A61B 17/20
[52] U.S. Cl. ............................ 604/22; 604/508; 604/523
[58] Field of Search .......................... 604/22, 49, 52–54, 604/164–165, 170, 264, 280, 283, 266, 267

[56] References Cited

U.S. PATENT DOCUMENTS

| | | | |
|---|---|---|---|
| 1,902,418 | 3/1933 | Pilgrim | 604/43 |
| 4,385,635 | 5/1983 | Ruiz . | |
| 4,690,672 | 9/1987 | Veltrup | 604/43 |
| 4,790,813 | 12/1988 | Kensey | 604/22 |
| 4,898,574 | 2/1990 | Uchiyma et al. | 604/22 |
| 4,913,698 | 4/1990 | Ito et al. | 604/22 |
| 5,114,399 | 5/1992 | Kovalcheck | 604/22 |
| 5,215,614 | 6/1993 | Wijkamp et al. . | |
| 5,221,270 | 6/1993 | Parker . | |
| 5,234,416 | 8/1993 | Macaulay et al. . | |
| 5,250,059 | 10/1993 | Andreas et al. . | |
| 5,300,022 | 4/1994 | Klapper et al. | 604/35 |
| 5,318,518 | 6/1994 | Plechinger et al. | 604/43 |
| 5,358,485 | 10/1994 | Vance et al. | 604/22 |
| 5,380,307 | 1/1995 | Chee et al. . | |
| 5,425,723 | 6/1995 | Wang et al. | 604/280 |
| 5,496,267 | 3/1996 | Drasler et al. | 604/22 |
| 5,792,167 | 8/1998 | Kablik et al. | 606/180 |

*Primary Examiner*—Wynn Wood Coggins
*Assistant Examiner*—LoAn H. Thanh
*Attorney, Agent, or Firm*—Hugh D. Jaeger

[57] ABSTRACT

A surgical device and method for removal of tissue, such as thrombus, from a vessel in the body. The device has a first tube with a distal open end and an inward directed stop and a second tube with an outward directed stop for engaging the inward directed stop and thereby regulating the relationship between a retrograde jet and the distal open end. Thrombus is dislodged, entrained, and broken into pieces which are evacuated through the first tube.

8 Claims, 23 Drawing Sheets

RHEOLYTIC THROMBECTOMY CATHETER AND METHOD OF USING SAME

BACKGROUND OF THE INVENTION

1. Field of the Invention

The present invention relates to a rheolytic thrombectomy catheter and method of using same to remove thrombus from a body vessel or other body cavity.

2. Description of the Prior Art

Procedures and apparatus have been developed for ease in removing tissue and various deposits. Several such devices employ a jet of saline as the working tool to help break up the tissue deposit and further provide a suction means to remove the deposit. U.S. Pat. No. 5,135,482 to Neracher describes a hydrodynamic device for removal of organic deposit from a human vessel. A supply of saline is delivered by a high pressure duct to the distal end of a catheter. The saline exits the duct as a jet that is directed generally forward and directly toward the tissue to be broken up. The duct is contained within and can move axially with respect to a hose that is positioned around the duct. A vacuum suction is applied to the hose to remove the debris that is created from the broken-up tissue. This device is not intended to pass through tortuous pathways found in the fragile vessels of the brain, and any attempt to employ the device for such purpose would be far too traumatic to the patient.

Another drainage catheter, described by Griep in U.S. Pat. No. 5,320,599, has a discharge channel and a pressure channel. The channels are formed into a single catheter tube such that the two tubes are fixed with respect to each other. This catheter could not provide the flexibility needed to negotiate the tortuous vascular pathways found in the vessels of the brain.

SUMMARY OF THE INVENTION

The general purpose of the present invention is to provide a rheolytic thrombectomy catheter and method of using same to remove thrombus from a body vessel or other body cavity.

The present invention, a rheolytic thrombectomy catheter, is a surgical device for removal of material such as thrombus from a vessel or other body cavity. As shown in one or more embodiments, a rheolytic thrombectomy catheter for removing tissue from a vessel or other body cavity includes an outer assembly comprising a first tube or guide catheter having a lumen with an open distal end and an internally and distally located stationary stop partially obstructing the lumen at the open distal end, the lumen being of a diameter sufficient to allow passage of a guidewire; and an inner assembly comprising a high pressure second tube or hypo-tube having a high pressure lumen and a distal end having one or more orifices, a distally located transitional stop fixed to the high pressure hypo-tube adjacent to the distal end, and means characterized as a jet cap positioned at and coacting with the hypo-tube distal end for directing one or more jets of saline toward the distal end of the guide catheter, the inner assembly being movable axially within the outer assembly such distally located transitional stop engages the stationary stop to hold the jet cap in a desired relationship with respect to the distal end of the guide catheter.

In another embodiment, a rheolytic thrombectomy catheter for removing thrombus or other body tissue from an obstructed body vessel or other body cavity includes an outer assembly including an evacuation tube having a proximal end and an open distal end containing a distally located stationary stop and having an evacuation lumen that is of a diameter sufficient to allow passage of a standard coronary or interventional neuroradiological guidewire; and an inner assembly including a high pressure hypo-tube having a high pressure lumen, the high pressure hypo-tube having a proximal end and a distal end, the distal end having one or more orifices through which saline can exit from the high pressure lumen to be directed toward the open distal end of the evacuation tube, a transitional stop fixed to the high pressure hypo-tube at a position closer to the distal end than to the proximal end, and and means characterized as a jet cap positioned at the distal end of the high pressure hypo-tube, the jet cap coacting with the high pressure hypo-tube to direct one or more jets of saline toward the open distal end of the evacuation tube.

Preferably, the rheolytic thrombectomy catheter has a guidewire coil attached at the distal end of the jet cap to allow advancement of the inner assembly and the outer assembly together within the vasculature. Preferably, the rheolytic thrombectomy catheter has a jet cap which directs a jet of saline toward the distal end of the guide catheter, which functions as an evacuation tube. Preferably, the rheolytic thrombectomy catheter includes a high pressure hypo-tube with at least one orifice and a jet cap configured and arranged for directing one or more jets of saline to impinge upon or near the distal end of the guide catheter. The rheolytic thrombectomy catheter preferably is flexible and can pass over a standard guidewire through tortuous vascular pathways.

The present invention also provides a method of removing thrombus from an obstructed body vessel. The method includes the steps of:

a. providing a guidewire and an outer assembly including a guide catheter having a distal end and an internally located stationary stop positioned adjacent to the distal end;

b. advancing the guidewire to a vascular site containing thrombus;

c. advancing the guide catheter over the guidewire to the vascular site containing thrombus to position the distal end at the vascular site;

d. removing the guidewire from the guide catheter;

e. providing an inner assembly including a hypo-tube carrying a jet cap and a transitional stop spaced apart from the jet cap;

f. advancing the inner assembly within the guide catheter of the outer assembly to engage the transitional stop with the stationary stop; and, g. providing a high pressure saline supply to the hypo-tube so as to cause a jet of saline to emanate from the jet cap and to impinge on thrombus and on or near the distal end of the guide catheter, thereby dislodging thrombus and entraining thrombus into the saline jet and thence into the guide catheter.

In the method, preferably, the jet cap carries a distally projecting guidewire coil to facilitate further distal advancement of the inner assembly and the outer assembly together within the vasculature to a further vascular site containing thrombus so as to remove additional distally situated thrombus.

The present invention is also a catheter combination including a first tube or guide catheter, being a part of an outer assembly, the first tube having a proximal end, an open distal end, and a lumen extending between the proximal end and the open distal end; a second tube or hypo-tube, being a part of an inner assembly, the second tube being separable from the first tube and being insertable within the lumen of the first tube, the second tube having a proximal end, a distal end, and a lumen extending between the proximal end and the distal end; a jet cap, being also a part of the inner assembly, the jet cap being connected to the second tube at the distal end of the second tube for directing fluid exiting the lumen of the second tube, the jet cap being capable of passage through the lumen of the first tube and being characterized by the ability to provide a localized region of low pressure associated with a liquid flow directed generally proximally and into the lumen of the first tube through the open distal end of the first tube when the jet cap is located and oriented appropriately relative to the open distal end of the first tube; and means for indexing an appropriate positional relationship of the jet cap and distal end of the second tube relative to the open distal end of the first tube. The means for indexing preferably includes a distally located stationary stop projecting inward from the first tube and a distally located transitional stop projecting outward from the second tube. When the second tube is advanced within the first tube, the stops mutually engage to control the orientation and spacing and relationship between the jet cap and the open distal end of the first tube. More preferably, the stops are each tapered to additionally laterally position the second tube within the first tube. Most preferably, the centering causes the tubes to become concentric. Preferably, one or both stops interact, when engaged, to preserve a channel for fluid flow rather than fully obstructing the cavity between the first tube and the second tube.

One significant aspect and feature of the present invention is the variously designed jet caps which are oriented to direct jets of saline in a proximal direction.

Another significant aspect and feature of the present invention is the stationary stop at the distal end of the guide catheter and the distally located transitional stop on the hypo-tube which together coact to position a jet cap at a defined distance beyond the distal end of the guide catheter.

Still another significant aspect and feature of the present invention is the distally located transitional stop which has an evacuation lumen and a hypo-tube receiving hole which is offset from the longitudinal axis of the distally located transitional stop.

Yet another significant aspect and feature of the present invention is the provision of complementary angled surfaces on the distally located stationary and transitional stops which upon engagement serve to center the inner assembly within the outer assembly.

A further significant aspect and feature of the present invention is the distally located stationary stop which is formed unitarily with the wall of the guide catheter at the distal end of the guide catheter.

A still further significant aspect and feature of the present invention is the guidewire coil provided at the distal end of the jet cap to allow advancement of the inner assembly and the outer assembly together within the vasculature.

Having thus described embodiments and significant aspects and features of the present invention, it is the principal object of the present invention to provide a rheolytic thrombectomy catheter and method of using same to remove thrombus from a body vessel.

One object of the present invention is to provide a rheolytic thrombectomy catheter of such size, flexibility and construction as to enable it to pass readily through the tortuous pathways found in the fragile vessels of the brain.

Another object of the present invention is to provide a rheolytic thrombectomy catheter with means for producing one or more jets of saline and projecting them in a proximal direction toward a site of thrombus and toward an evacuation passage.

Yet another object of the present invention is to provide a rheolytic thrombectomy catheter with means for producing one or more jets of saline and with indexing means to position the jet producing means at a prescribed location at the distal end of the catheter.

Still another object of the present invention is to provide a rheolytic thrombectomy catheter of the type having an inner assembly that is insertable into an outer assembly with stop means for limiting the extent to which the inner assembly can be inserted into the outer assembly.

A further object of the present invention is to provide a rheolytic thrombectomy catheter of the type having an inner assembly and an outer assembly with means which centers the inner assembly within the outer assembly and which orients the parts of the inner assembly in a prescribed manner with respect to the parts of the outer assembly.

A still further object of the present invention is to provide an improved method of removing thrombus from an obstructed body vessel.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
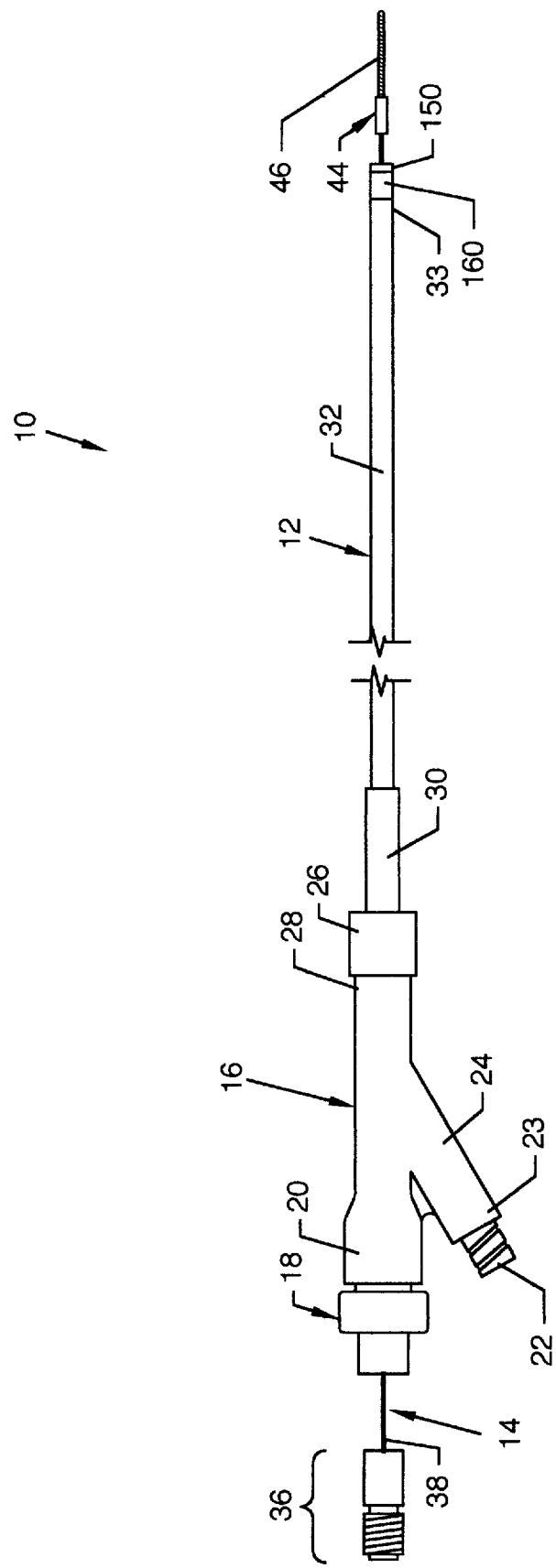
FIG. 1 is a side view of the present invention, a rheolytic thrombectomy catheter useful for the removal of thrombus.
Figure 2:
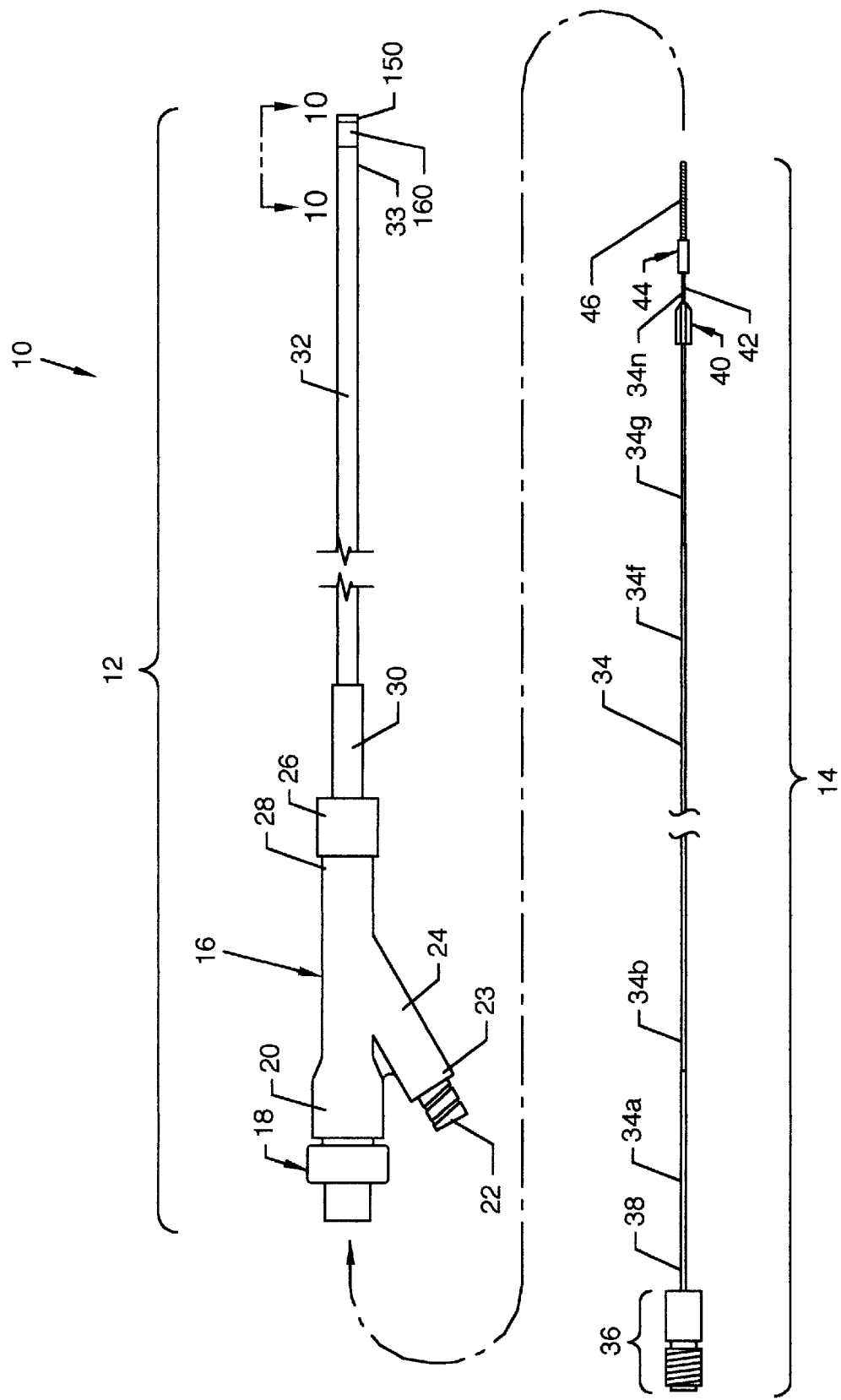
FIG. 2 is a semi-exploded side view of the rheolytic thrombectomy catheter depicting the two major assemblies thereof, viz., an outer assembly and an inner assembly.

FIG. 1 illustrates a side view of a rheolytic thrombectomy catheter 10 useful for the removal of thrombus, and FIG. 2 illustrates a semi-exploded side view of the rheolytic thrombectomy catheter 10. The rheolytic thrombectomy catheter 10 includes two major assemblies: namely, an outer assembly 12 and an inner assembly 14. The inner assembly 14 aligns concentrically to and within the outer assembly 12 and extends beyond the length of the outer assembly 12. Externally visible components, or portions of components, of the outer assembly 12 of the rheolytic thrombectomy catheter 10, as illustrated in FIGS. 1 and 2, include a manifold 16, also known as a Y-adapter, a hemostasis nut 18 secured in the proximal end 20 of the manifold 16, a Luer connection 22 located at the proximal end 23 of an angled manifold branch 24 extending from the manifold 16, a Luer fitting 26 secured to the distal end 28 of the manifold 16, a strain relief 30 secured to the distal end 28 of the manifold 16 by the Luer fitting 26, and a first tube or guide catheter 32, having a distal end 33, secured to the manifold 16 by the strain relief 30 and Luer fitting 26. The externally visible components of the inner assembly 14, illustrated in FIG. 2, include a high pressure second tube or hypo-tube 34, a filter housing/high pressure connection assembly 36 concentrically aligned to and secured over and about the hypo-tube proximal end 38, a configured transitional stop 40 concentrically aligned to and secured over and about the hypo-tube 34 at a point near and adjacent to the hypo-tube distal end 42, a jet cap 44 concentrically aligned to and secured over and about the hypo-tube 34 at the hypo-tube distal end 42, and a guidewire coil 46 concentrically aligned to and secured to one end of the jet cap 44. The high pressure hypo-tube 34 is drawn and is tapered in incremental steps to provide degrees of flexibility along its length. For purposes of example and illustration, the hypo-tube 34 can include a hypo-tube portion 34a at the hypo-tube proximal end 38 having an outer diameter of 0.018 inch or smaller, and can include a plurality of incrementally stepped down hypo-tube portions 34b–34n each of lesser outer diameter, where the last hypo-tube portion 34n is stepped down to an outer diameter .008 inch at the hypo-tube distal end 42. The hypo-tube 34 becomes increasingly more flexible from the hypo-tube proximal end 38 towards the hypo-tube distal end 42 due to the incremental diameter decrease along its length. Increasing flexibility along the length of the hypo-tube 34 allows for easier flexed penetration into tortuous vascular paths. Although the hypo-tube 34 is stepped down in increments, the hypo-tube 34 can also be fashioned of a constantly decreasing outer diameter to provide increasing flexibility along its length and shall not be construed to be limiting to the scope of the invention.

Figure 3:
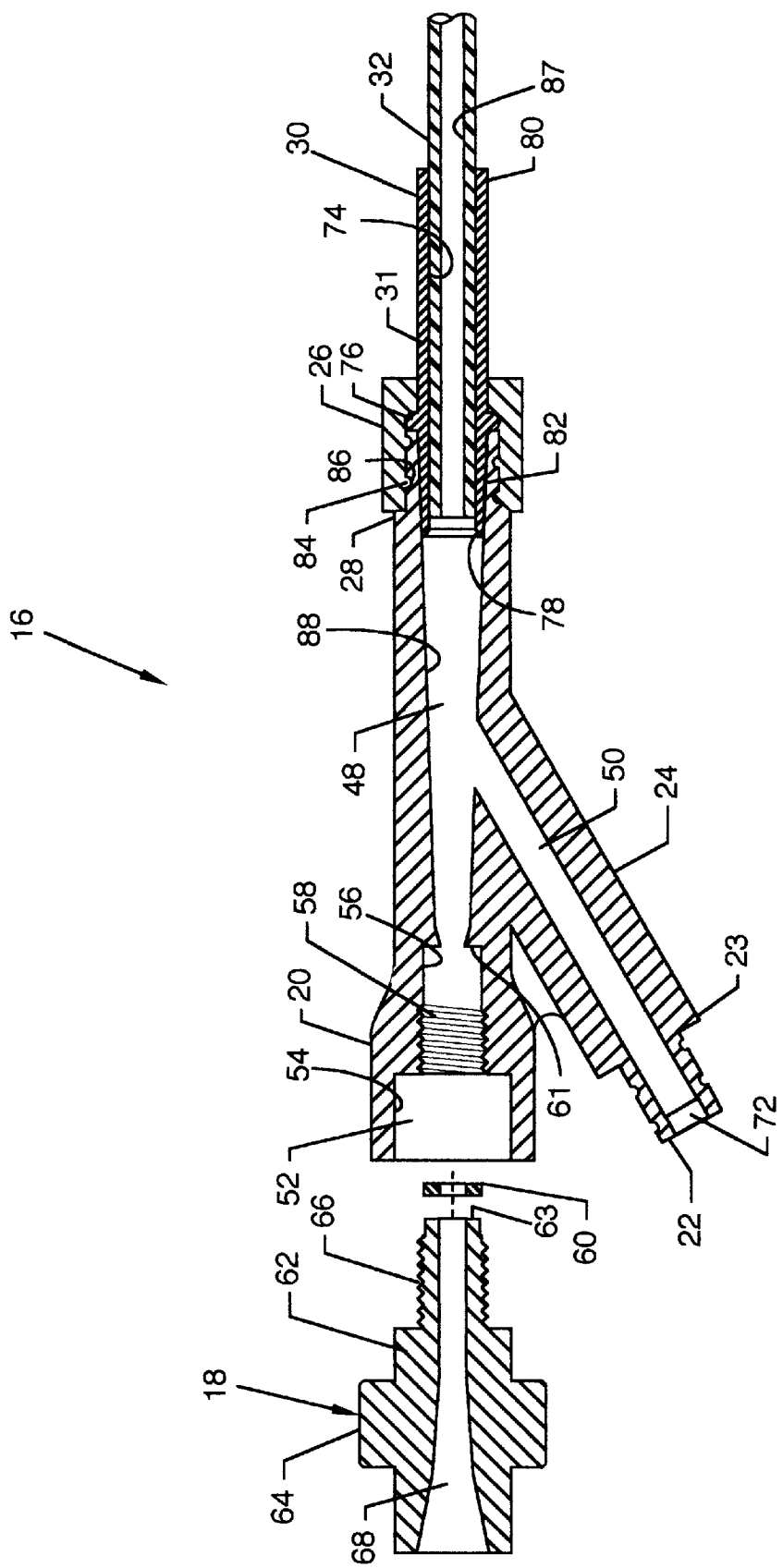
FIG. 3 is a semi-exploded cross sectional side view of a manifold and adjacent components constituting parts of the outer assembly.

FIG. 3 illustrates a semi-exploded cross sectional side view of the manifold 16 and adjacent components, where all numerals correspond to those elements previously described. The manifold 16 includes a tapered centrally located passage 48 aligned along the longitudinal axis of the manifold 16 and a branch passage 50 extending along the axis of the branch 24 which intersects and is connected to the central passage 48. The manifold proximal end 20 houses a multi-radius cavity 52 including a round outer cavity portion 54 and a connected round inner and smaller cavity portion 56 having a threaded surface 58 on the proximal portion thereof. The hemostasis nut 18 includes a body 62 having a grasping surface 64 extending thereabout, a threaded surface 66 extending from the body 62, an annular surface 63 at the end of the threaded surface 66, and a passageway 68 aligned centrally to the longitudinal axis of the hemostasis nut 18. The passageway 68 has a wide radius at the proximal end which decreases toward the distal end. The initial wide radius is helpful for insertion of the inner assembly 14 or guidewires and the like. A seal 60 aligns to the distally located annular surface 61 of the round inner cavity portion 56 and bears against the annular surface 63 of the hemostasis nut 18 to seal the central passage 48 of the manifold 16 to the passageway 68 in the hemostasis nut 18. The multi-radius cavity 52 and its internal geometry accommodate corresponding geometry of the hemostasis nut 18 and the seal 60. Luer connection 22 extends from the angled manifold branch proximal end 23. A filter 72 aligns at the mouth of the branch passage 50. The filter 72 and a Luer fitting (not illustrated) can be used to prevent any particulate outflow, to provide for metered outflow, or, alternatively, to provide suction for fluid or particle evacuation.

Luer fitting 26 is utilized to secure the strain relief 30 and the guide catheter 32 to the distal manifold end 28. The strain relief 30 is comprised of a tube 31, a central bore 74 internal to the tube 31 which accommodates the guide catheter 32, an annular flange 76 about the tube 31, and a tapered proximal tube mouth end 78. It is noted that the outer diameter of the tube 31 is constant from the annular flange 76 to the distal tube end 80, and that the outer diameter steadily decreases from the annular flange 76 to the tapered proximal tube mouth end 78 to provide a tapered tube surface 82 which conforms, for purpose of a proper fit, to the taper of the tapered central passage surface 88 of the central passage 48. The tapered proximal tube mouth end 78 allows for easily accomplished alignment of guidewires and other assemblies, such as inner assembly 14 and the like, with a lumen 87 located in the guide catheter 32. The Luer fitting 26 includes threads 84 which threadingly engage corresponding threads 86 at the distal end 28 of the manifold 16. The Luer fitting 26 bears against the annular flange 76 of the strain relief 30 to force the tapered tube surface 82 of the strain relief 30 against the tapered central passage surface 88 of the central passage 48 to effect a suitable seal.

Figure 4:
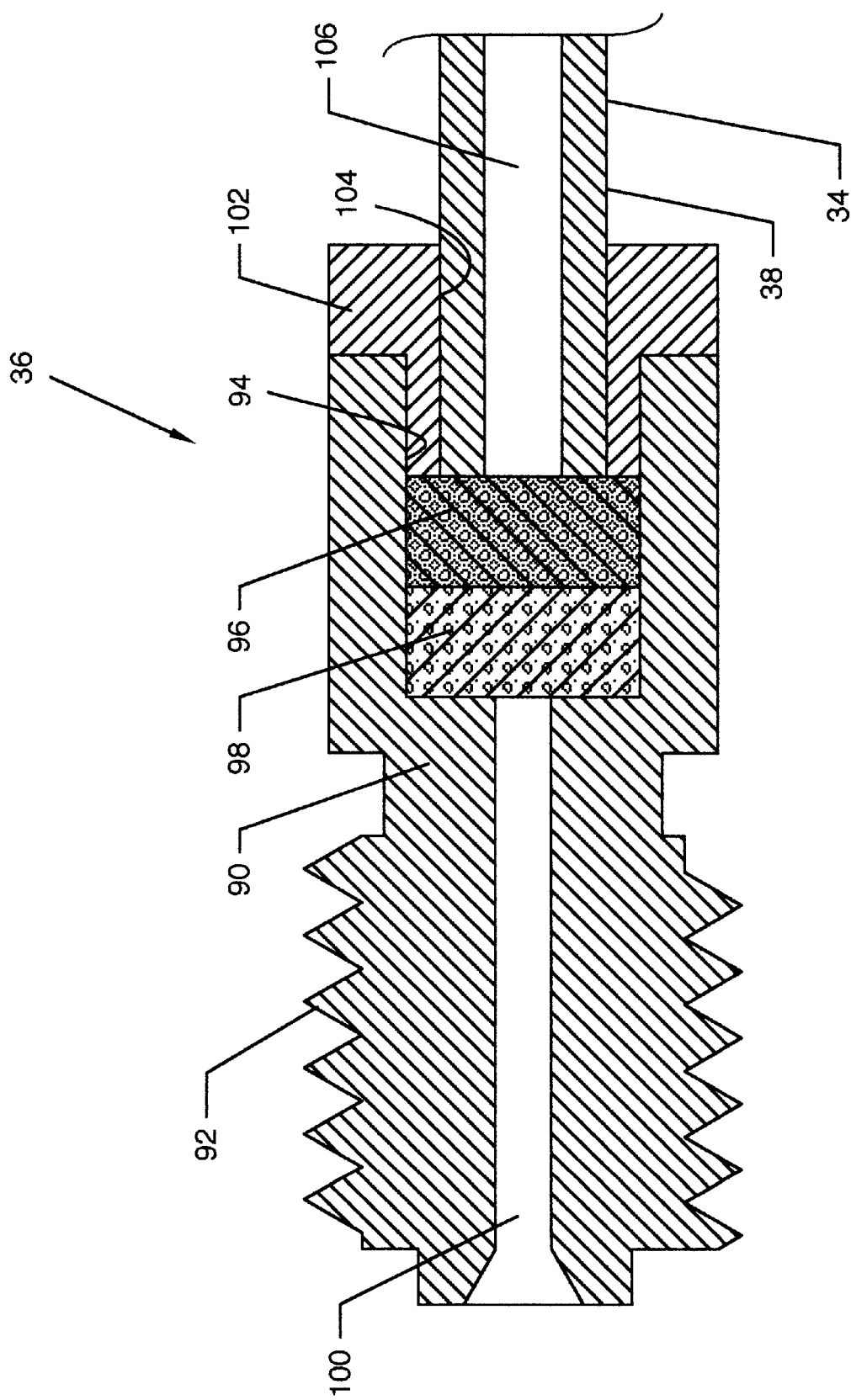
FIG. 4 is a longitudinal sectional view of a filter housing/ high pressure connection assembly attached to the proximal end of a hypo-tube, shown only partially.

FIG. 4 illustrates a longitudinal sectional view of the filter housing/high pressure connection assembly 36 located at the hypo-tube proximal end 38 of the hypo-tube 34, where all numerals correspond to those elements previously described. The filter housing/high pressure connection assembly 36 includes a cylindrical-like body 90 having a threaded surface 92, a tubular cavity 94, fine and course filters 96 and 98 residing in the tubular cavity 94, a central passage 100 extending through the body 90 and connecting to the tubular cavity 94, and a plug-like cap 102, having a central bore 104, extending into the tubular cavity 94 of the body 90. The hypo-tube 34 suitably secures within the central bore 104 of the cap 102. The central passage 100 communicates through fine and course filters 96 and 98 with the lumen 106 of the hypo-tube 34.

Figure 5:
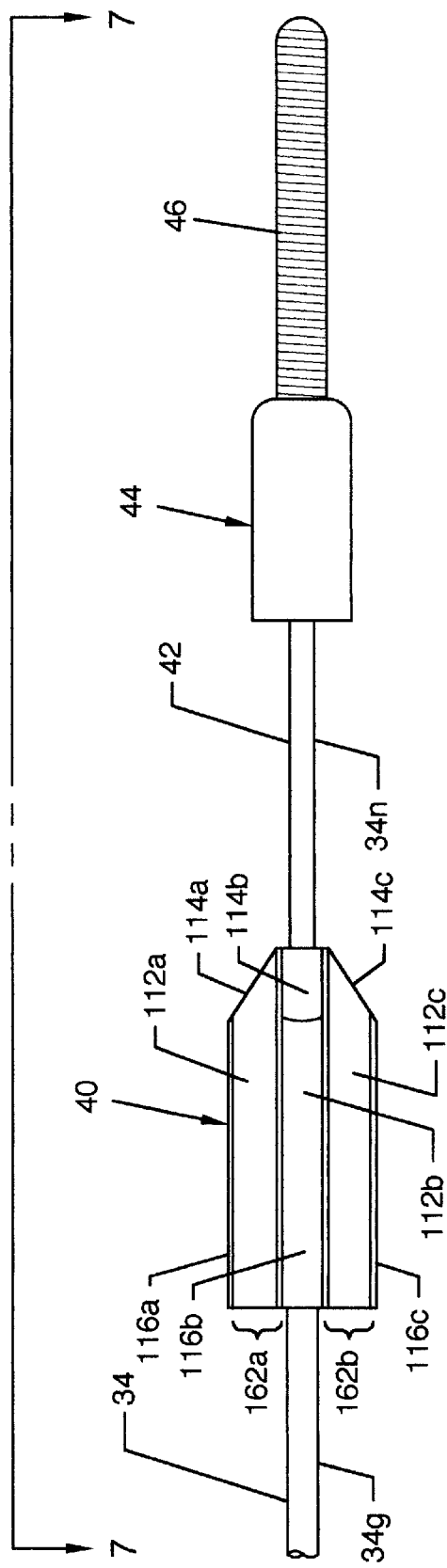
FIG. 5 is a side view of a transitional stop, a jet cap, and a guidewire coil aligned over and about the hypo-tube at the distal end thereof.

FIG. 5 illustrates a side view of the transitional stop 40, the jet cap 44 and the guidewire coil 46 aligned over and about the hypo-tube 34 near or at the hypo-tube distal end 42, where all numerals correspond to those elements previously described. The relative sizes of the transitional stop 40 and the jet cap 44 with respect to each other and with respect to the sizes of the lumen 87 of the guide catheter 32 and a stationary stop 150 residing in the guide catheter 32, as well as details of the transitional stop 40, are discussed in detail below with relation to FIGS. 6, 12 and 13.

Figure 6:
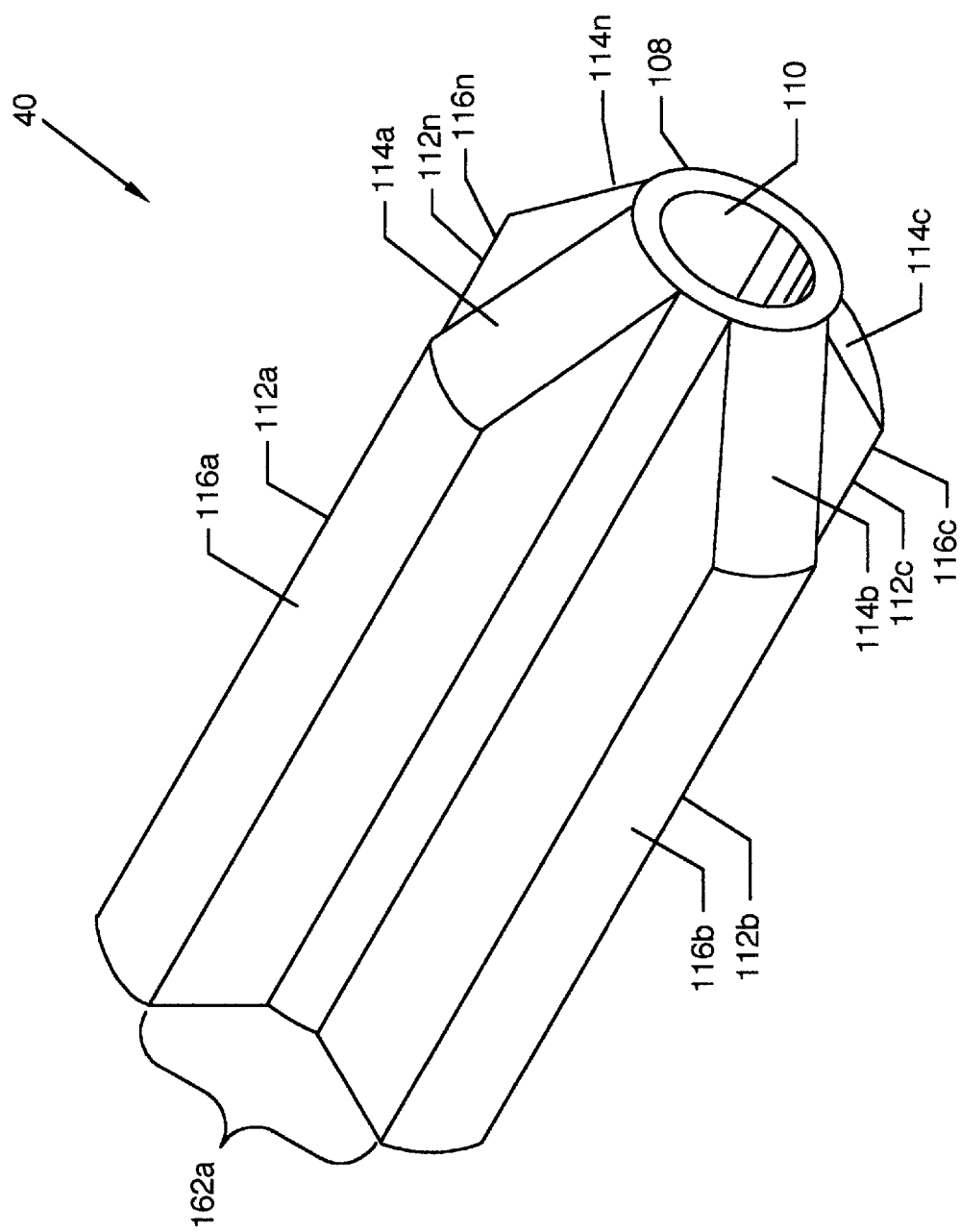
FIG. 6 is an isometric view of the transitional stop.

FIG. 6 illustrates an isometric view of the transitional stop 40, where all numerals correspond to those elements previously described. The one-piece transitional stop 40 includes a tubular body 108 having a central bore 110 and a plurality of guide bars 112a–112n extending radially from the tubular body 108. Guide bars 112a–112n include angled leading edges 114a–114n extending from the leading portion of the body 108 to arced surfaces 116a–116n. The angled leading edges 114a–114n contact a stationary stop 150 in the guide catheter 32, as later described in detail. Preferably, and for purposes of example and illustration, the arced surfaces 116a–116n describe arcs centered on the longitudinal axis of the tubular body 108; but, in the alternative, the arced surfaces 116a–116n could describe arcs having other centers, or the surfaces could be flat or be of other geometric design, and shall not be construed to be limiting to the scope of the invention.

Figure 7:
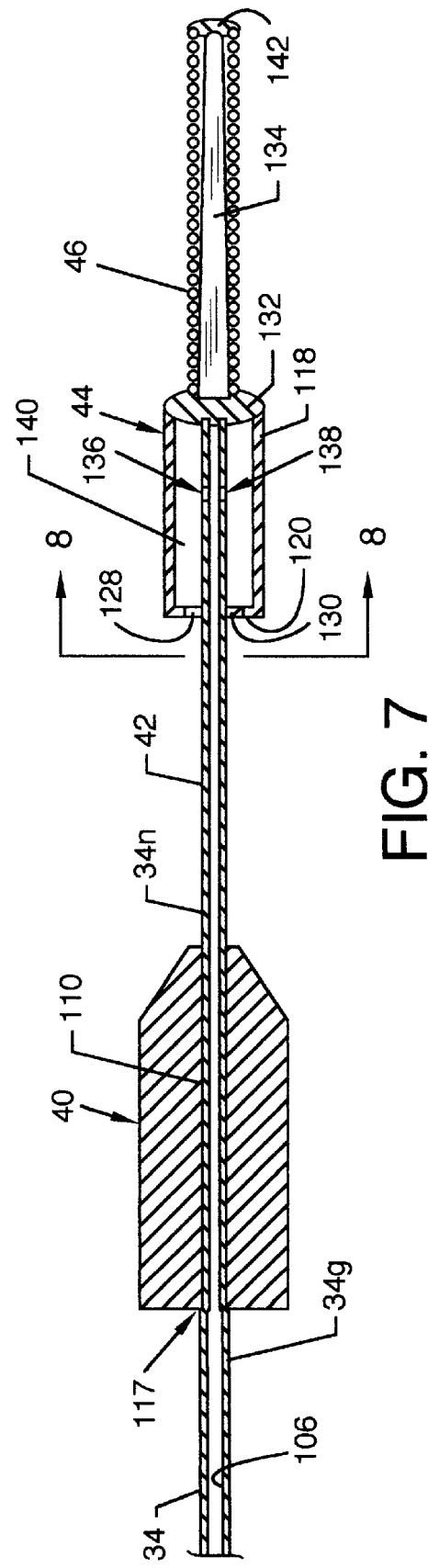
FIG. 7 is a longitudinal sectional view taken along line 7—7 of FIG. 5.
Figure 8:
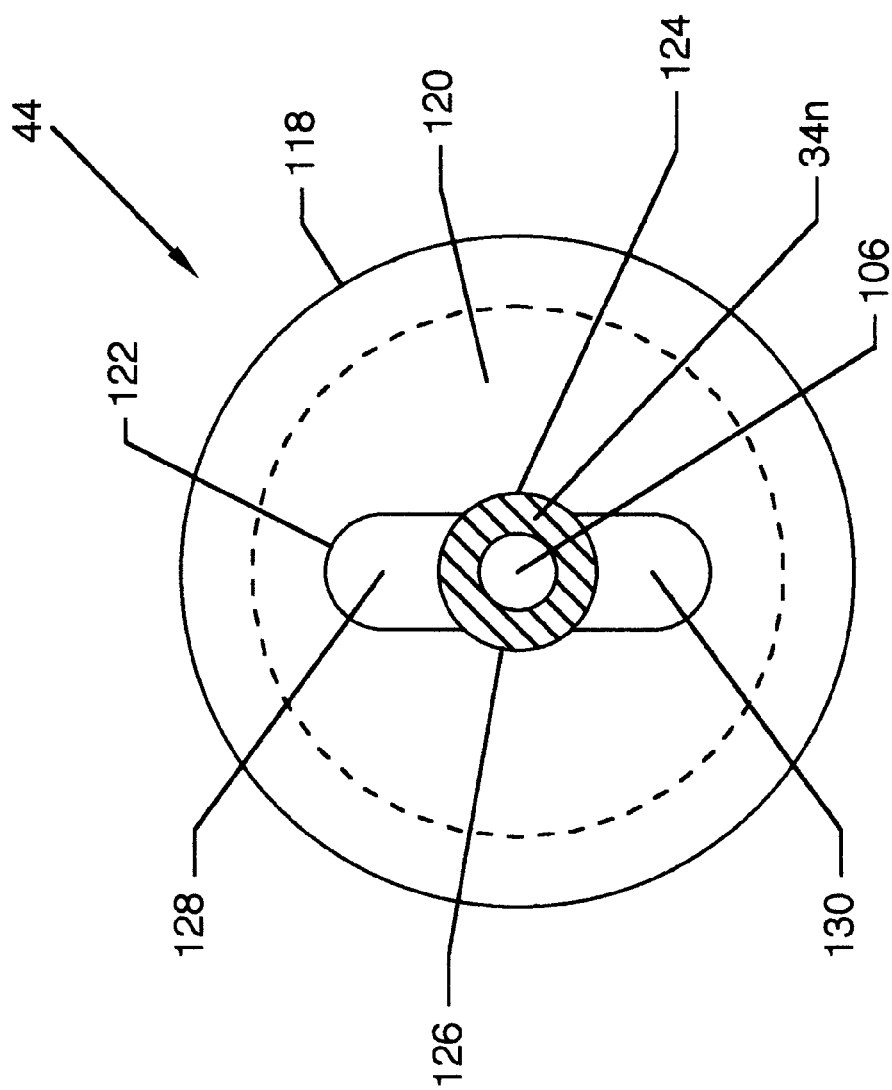
FIG. 8 is a view of the proximal end of the jet cap on the hypo-tube looking in the direction of line 8—8 of FIG. 7, with the hypo-tube shown in cross section.

FIG. 7 illustrates a longitudinal sectional view, taken along line 7—7 of FIG. 5, of the transitional stop 40, the jet cap 44 and the guidewire coil 46 aligned and secured over and about the hypo-tube 34 near or at the hypo-tube distal end 42; and FIG. 8 illustrates a view of the jet cap 44 looking in the direction of line 8—8 of FIG. 7, where all numerals correspond to those elements previously described. The central bore 110 of the transitional stop 40 is aligned and appropriately secured over and about the last hypo-tube portion 34n to affix the transitional stop 40 over and about and near the hypo-tube distal end 42. The proximal end of the transitional stop 40 juxtaposes and abuts the shoulder-like transition 117 between the next to the last hypo-tube portion 34g and the last hypo-tube portion 34n. The jet cap 44 aligns over and about and is secured to the last hypo-tube portion 34n at the hypo-tube distal end 42. As shown in FIGS. 7 and 8, the jet cap 44 is tubular and includes a circular peripheral wall 118 and a circular end wall 120 extending inwardly from one end of the circular peripheral wall 118. Central to the circular end wall 120 is an elongated hole 122 having arcuate ends and opposite sides each having an arcuate mid section and straight portions extending oppositely from the arcuate mid section to the opposite arcuate ends, as shown in FIG. 8. The arcuate mid sections of the opposite sides of the elongated hole 122 are positioned at the center of the elongated hole 122 and are defined by opposing aligned arcuate portions 124 and 126 of common radius. The last hypo-tube portion 34n aligns to and extends through the center of the elongated hole 122 and is embraced by the arcuate portions 124 and 126, thereby dividing the elongated hole 122 into two jet orifices 128 and 130, the jet orifice 128 being defined by the portion of elongated hole 122 to one side of the outer surface of the last hypo-tube portion 34n, and the jet orifice 130 being defined by the portion of elongated hole 122 to the other side of the outer surface of the last hypo-tube portion 34n. At the distal end of the circular peripheral wall 118 is a weld 132 which joins together the circular peripheral wall 118, the extreme tip of the distal end 42 of the hypo-tube 34, the guidewire coil 46 and a tapered core 134. A plurality of orifices including orifices 136 and 138 in the distal end 42 of hypo-tube 34 align within the central cavity 140 of the jet cap 44 for fluid communication from lumen 106 to the central cavity 140 and to the two jet orifices 128 and 130. A weld 142 is also included at the distal end of the guidewire coil 46 to secure the end of the tapered core 134 to the guidewire coil 46 and to provide for smooth entry into a vessel or other body cavity.

Figure 9:
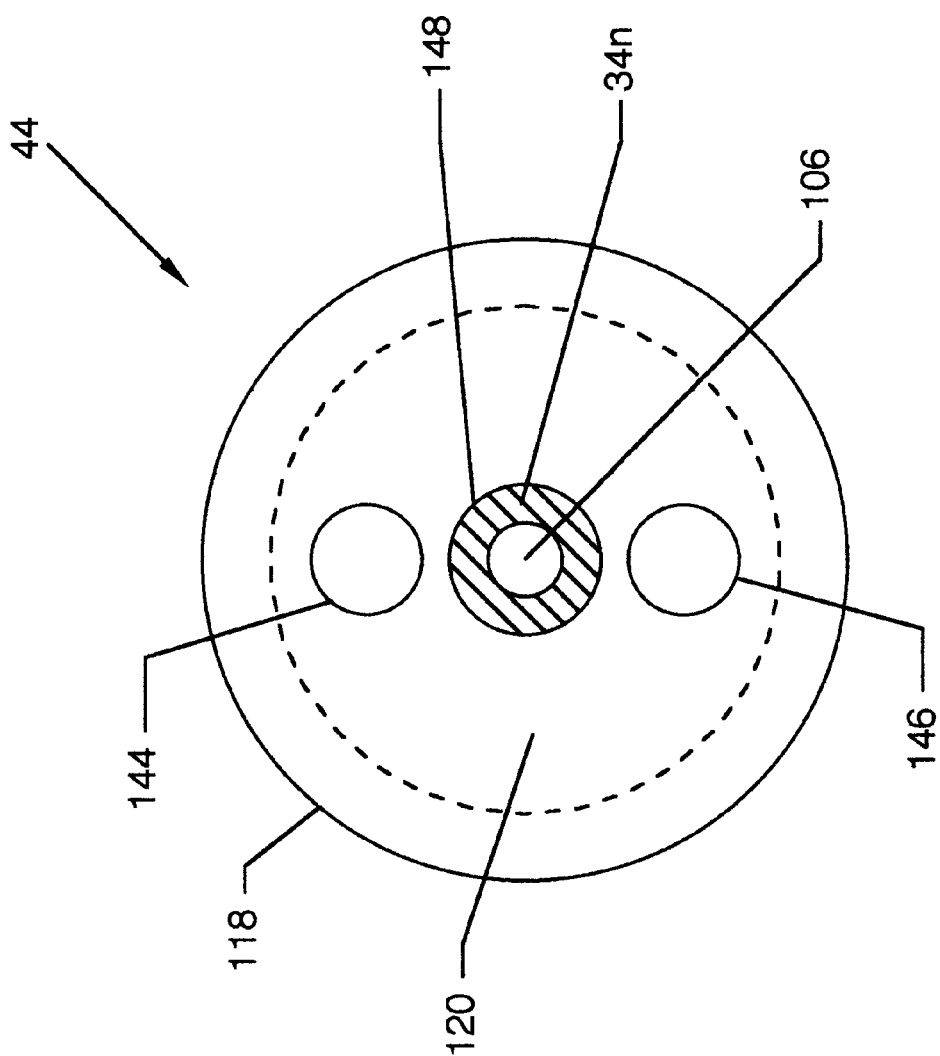
FIG. 9 is a view similar to FIG. 8 illustrating a slightly modified version of the jet cap.

FIG. 9 illustrates a slightly modified version of the jet cap 44 wherein two distinct jet orifices 144 and 146 are included in the circular end wall 120 in lieu of the elongated hole 122 shown in FIG. 8, and wherein a bore 148 in the circular end wall 120 accommodates the last hypo-tube portion 34n.

Figure 10:
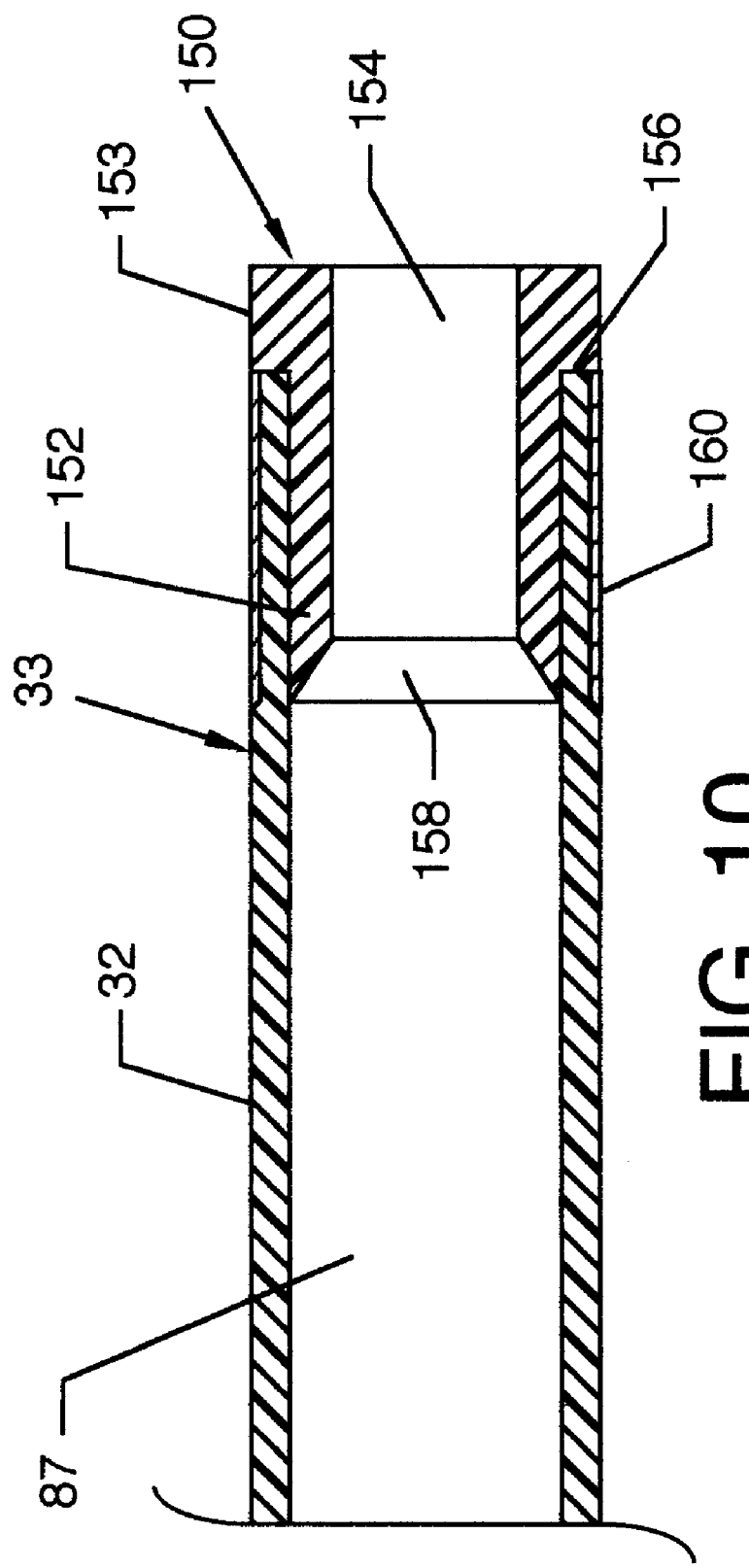
FIG. 10 is a longitudinal sectional view of the guide catheter distal end taken along line 10—10 of FIG. 2.

FIG. 10 illustrates a longitudinal sectional view of the guide catheter distal end 33 of the guide catheter 32 taken along line 10—10 of FIG. 2, where all numerals correspond to those elements previously described. Illustrated in particular is the multi-radiused stationary stop 150 frictionally engaging the lumen 87 at the guide catheter distal end 33. One outer radius defines the cylindrical body 152, which frictionally engages lumen 87, and another larger outer radius defines a cap 153 at the end of the stationary stop 150. A central bore 154 aligns coaxially within the cylindrical body 152 and the cap 153. An annular shoulder 156 between the cap 153 and the cylindrical body 152 abuts and aligns to the guide catheter distal end 33. An angled annular surface 158, which is complementary to the angled leading edges 114a–114n of the transitional stop 40 shown in FIG. 6, is included at the proximal end of the cylindrical body 152. An annular crimp sleeve 160 applied over and about the guide catheter distal end 33 ensures a positive fixation of the stationary stop 150 in the lumen 87.

Figure 11:
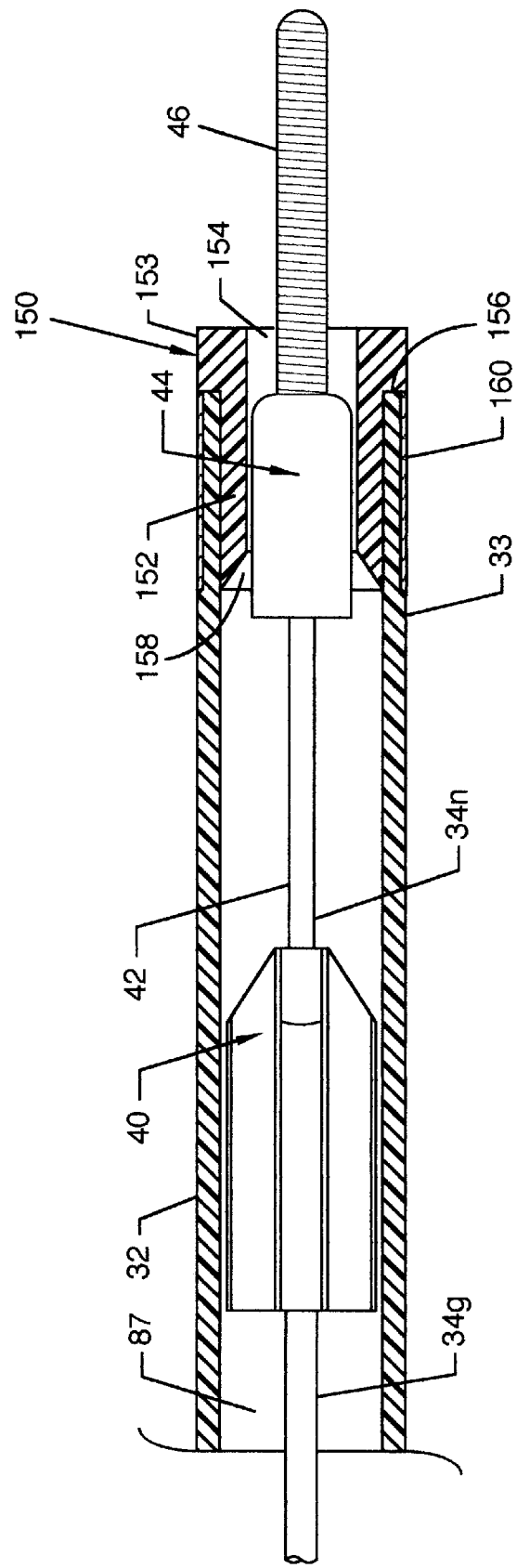
FIG. 11 is a longitudinal sectional view of the guide catheter distal end with the transitory stop, the jet cap, and the guidewire coil on the hypo-tube shown advancing therethrough.

FIG. 11 illustrates a longitudinal sectional view of the guide catheter distal end with the jet cap 44 transiting the central bore 154 of the stationary stop 150 and with the transitional stop 40 aligned within the lumen 87 of the guide catheter 32, where all numerals correspond to those elements previously described.

Figure 12:
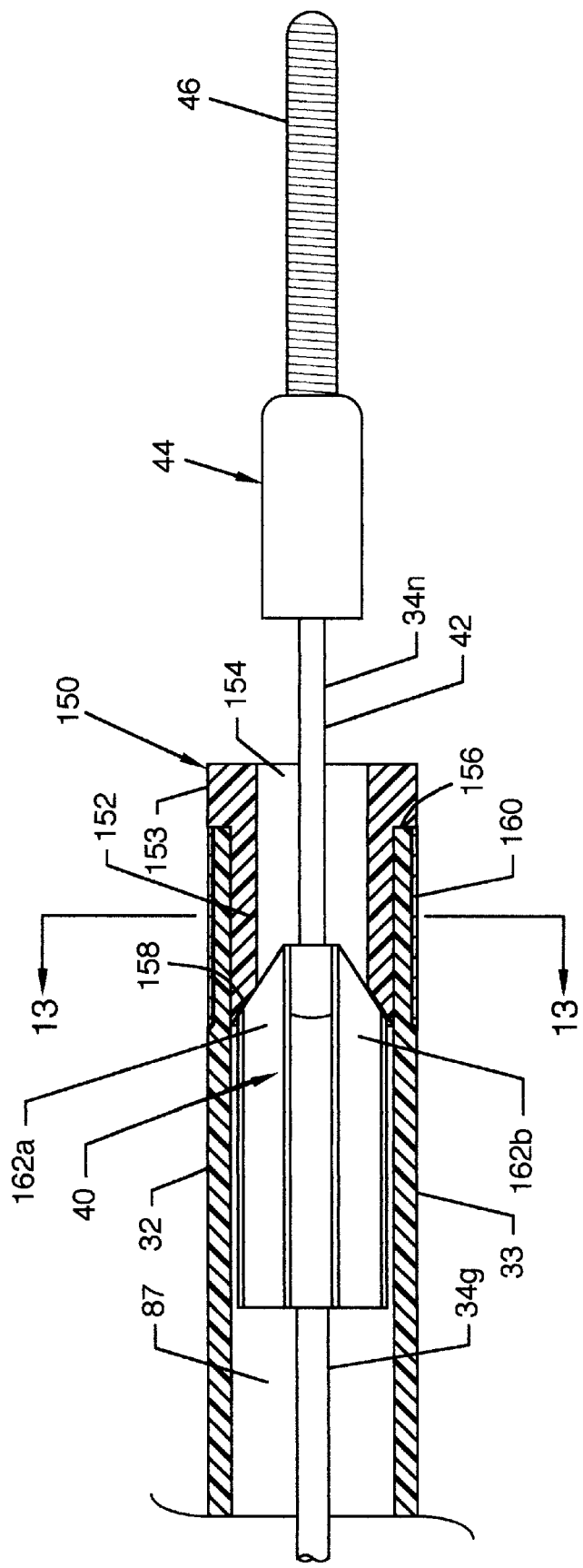
FIG. 12 is a longitudinal sectional view of the guide catheter distal end with the transitory stop, the jet cap, and the guidewire coil on the hypo-tube shown in final advanced position.

FIG. 12 illustrates a longitudinal sectional view of the guide catheter distal end with the transitional stop 40 aligned within the lumen 87 of the guide catheter 32 and in mutual engagement with the stationary stop 150, where all numerals correspond to those elements previously described. Mutual engagement of the stationary stop 150 with the transitional stop 40 positions the jet cap 44 at a desirable and finite distance from the stationary stop 150 at the guide catheter distal end 33.

Tubular guide catheter 32 may be constructed of a flexible polymer material and is characterized by an ability to follow over a flexible guidewire through the vasculature of a patient to be treated. Since the tubular guide catheter 32 may also be subjected to reduced or vacuum pressures in some applications, the tubular guide catheter 32 should be resistant to collapse or bursting at the pressure differentials employed. Again, for purposes of example and illustration, the guide catheter 32 can have an outer diameter of about 4 French or smaller, or an outer diameter of about 0.040 inch, and an inner diameter of about 0.028 inch which can also taper in diameter. As is well known in the art, the guide catheter 32 may be advanced and maneuvered through the vasculature such that the guide catheter distal end 33 may be selectively positioned adjacent to the site of desired surgical action, for example, adjacent to a thrombus obstructing a blood vessel.

The stationary stop 150 may be formed from a variety of materials. Preferably, the stationary stop 150 is formed of material identical to that of the guide catheter 32.

The transitional stop 40 is mounted in the hypo-tube 34 at a location spaced apart from the hypo-tube distal end 42 and distal from the hypo-tube portion 34g. The transitional stop 40 has a cross sectional extent such that it may not freely pass the stationary stop 150. The transitional stop 40 has a substantially X-shaped cross section when viewed axially, as in FIG. 13, which allows for fluid passage in a proximal direction. However, as will be discussed subsequently, numerous alternative shapes might be employed for the transitional stop 40 provided that at least passage of the transitional stop past the stationary stop 150 is prevented. Preferably, the distal portion of the transitional stop 40 includes tapered surfaces, such as angled leading edges 114a–114n. The jet cap 44 presents a cross section capable of passing through the central bore 154 of the stationary stop 150. The angled leading edges 114a–114n serve, in juxta-position with the angled annular surface 158 of the stationary stop 150, to desirably longitudinally position the transitional stop 40 relative to the stationary stop 150. The close longitudinal alignment of the plurality of guide bars 112a–112n within the lumen 87 of the guide catheter 32 generates lateral spaced relations, such as, for example, a concentric relationship between the first tube or guide catheter 32 and the second tube or hypo-tube 34, respectively. Preferably, the cross sectional extent of the transitional stop 40 is roughly about 0.010 inch to about 0.030 inch; however, the critical consideration in cross sectional dimensions of the transitional stop 40 is that it must pass through the lumen 87 of the first tube or guide catheter 32 and yet not pass the stationary stop 150.

The jet cap 44 is mounted at the distal end 42 of the hypo-tube 34 and includes a guidewire coil 46 extending distally from the jet cap 44. In a preferred embodiment, the jet cap 44, guidewire coil 46 and transitional stop 40 are radially symmetrical about the longitudinal extent of the hypo-tube 34. In such an embodiment, the jet cap 44 preferably has a diameter of from about 0.010 inch to about 0.030 inch. The hypo-tube 34 preferably has an outer diameter of about 0.008 inch to about 0.018 inch and also includes a continuous high pressure lumen 106 extending from the hypo-tube proximal end 38 to the hypo-tube distal end 42 and continuing into the jet cap 44. When the hypo-tube distal end 42 of the hypo-tube 34 is advanced through the lumen 87 of the guide catheter 32, the guidewire coil 46 and the jet cap 44 and any portion of the hypo-tube 34 distal from the transitional stop 40 are free to pass the location of the stationary stop 150. However, passage of the transitional stop 40 is prevented by the partial obstruction of the lumen 87 of guide catheter 32 by the stationary stop 150. Thus, when the distal angled leading edges 114a–114n of the transitional stop 40 engage the angled annular surface 158 of the stationary stop 150, a desired longitudinal relationship is dependably generated between the jet cap 44 and the guide catheter distal end 33 (at the cap 153) of the guide catheter 32. Most importantly, the jet cap 44 is oriented and spaced apart and distally situated at a desired relationship to the guide catheter distal end 33 of the guide catheter 32.

The jet cap 44 is preferably rounded or tapered at the distal end to facilitate advancement of the hypo-tube 34 and to avoid catching or snagging on the interior of the guide catheter 32, on the stationary stop 150, or on a vessel wall when advanced beyond the guide catheter distal end 33.

Fluid communication between the lumen 87 and the central bore 154 of the stationary stop 150 is allowed longitudinally and in a distal direction about the geometry of the transitional stop 40. As partially shown in FIGS. 5 and 6 and as fully shown in FIG. 13, longitudinally oriented passages 162a–116n are formed. For example, passage 162a is formed between guide bars 112a and 112b and a portion of the periphery of transitional stop body 108 extending from the proximal region of the transitional stop 40 distally toward and including the angled leading edges 114a–114b. Longitudinally oriented passages 162b–162n are formed in a corresponding fashion. Note particularly that a portion of the lumen 87 remains open where the transitional stop 40 interacts with the stationary stop 150 to allow passage of liquid and small portions of suspended tissue proximally through the guide catheter 32.

Figure 13:
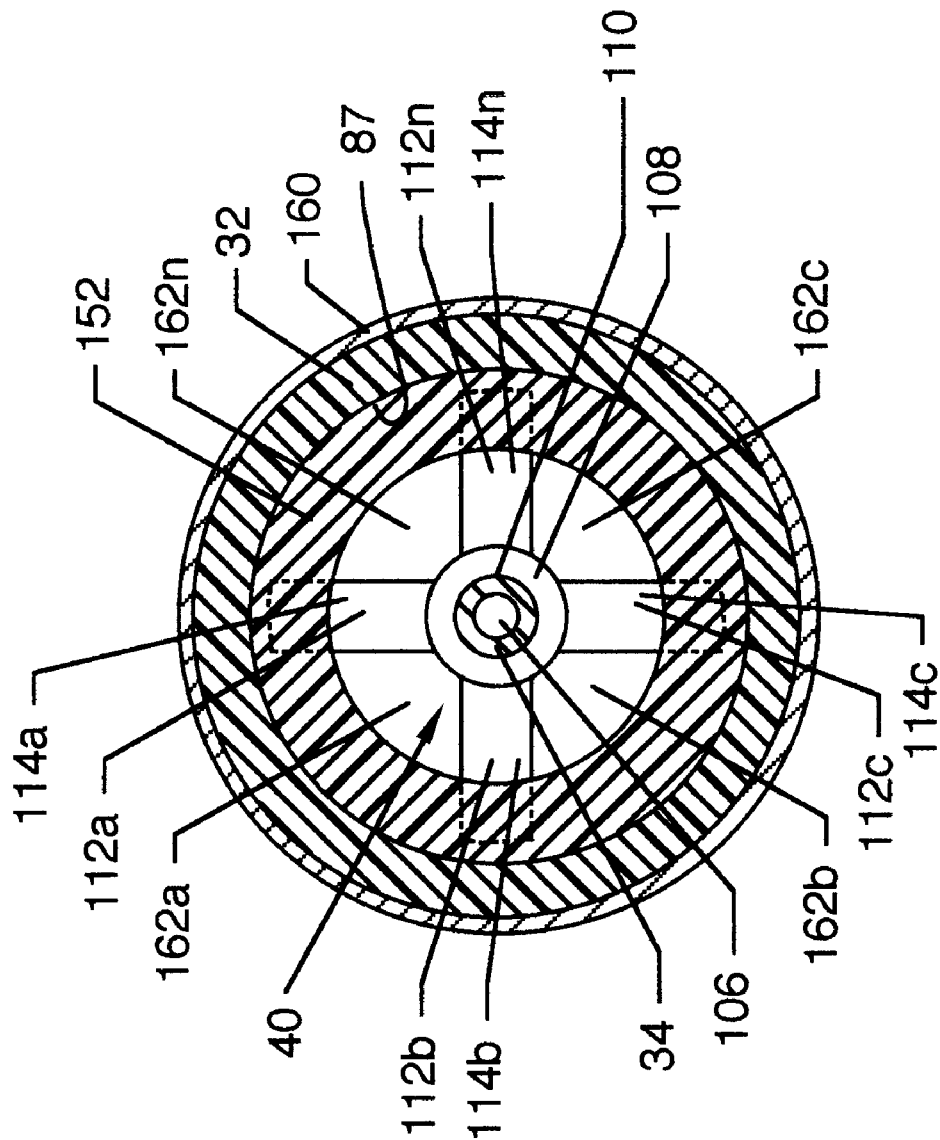
FIG. 13 is a cross-sectional view taken along line 13—13 of FIG. 12.

FIG. 13 illustrates a cross sectional view of the guide catheter distal end 33 taken along line 13—13 of FIG. 12, where all numerals correspond to those elements previously described. Illustrated in particular are the plurality of passages 162a–162n about the transitional stop 40 which allow passage of liquid and small portions of suspended tissue proximally through the lumen 87 of the guide catheter 32. Although the guide bars 112a–112n include planar side surfaces, other configurations having a rounded intersection or even having non-planar intersecting walls or other variations of longitudinal passages can be utilized and shall not be construed to be limiting to the scope of the invention.

Mode of Operation

Figure 14:
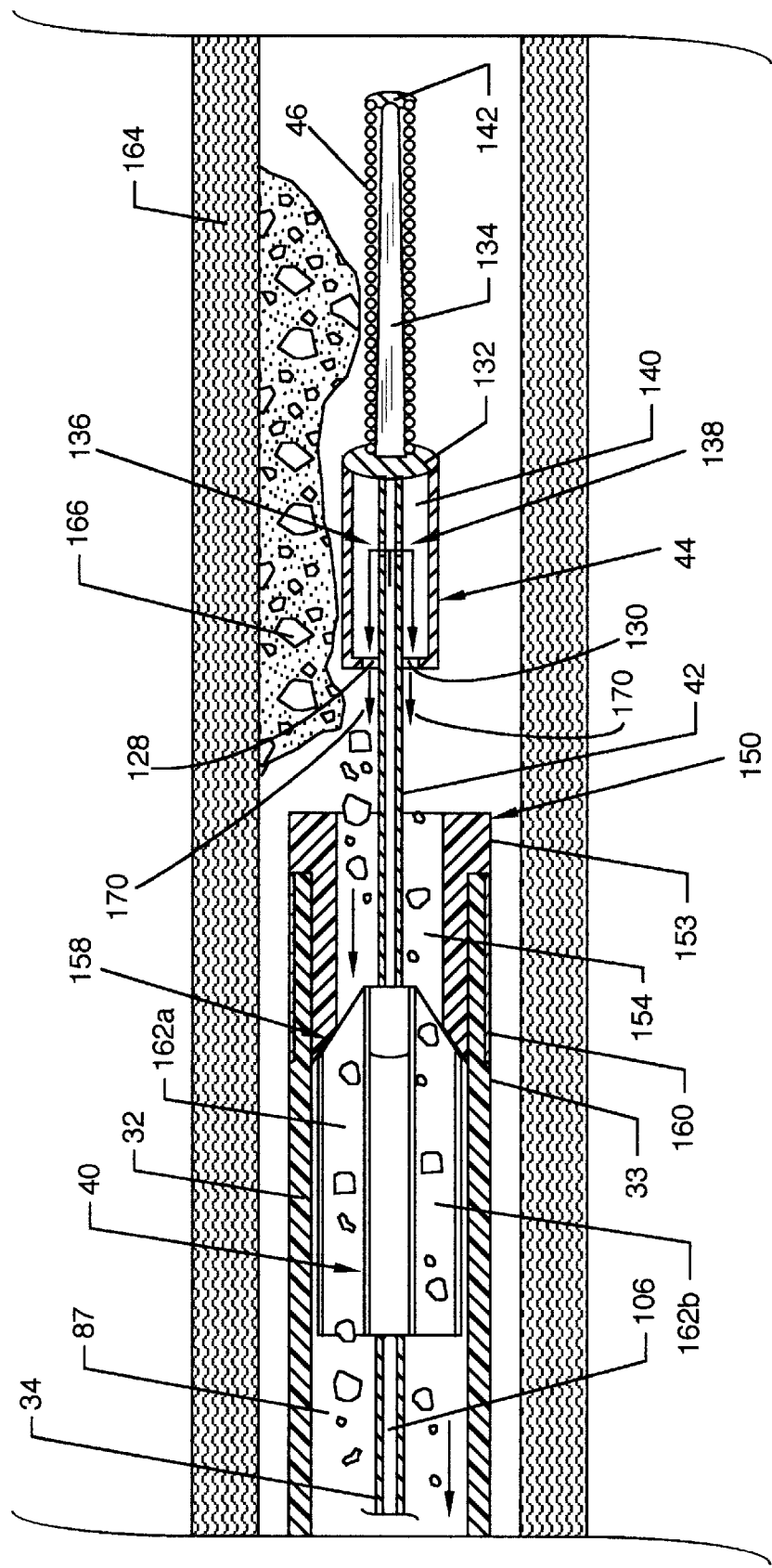
FIG. 14 is presented to illustrate schematically the mode of operation of the rheolytic thrombectomy catheter, and is a longitudinal sectional view depicting the distal end of the rheolytic thrombectomy catheter within a blood vessel at the site of a thrombotic deposit and lesion.

FIG. 14 best illustrates the mode of operation of the rheolytic thrombectomy catheter 10 with particular attention to the guide catheter distal end 33 and jet cap 44 positioned in a blood vessel 164, artery or the like at the site of a thrombotic deposit and lesion 166.

A guidewire is first advanced percutaneously through the vasculature to the site of the thrombotic deposit and lesion 166. For a distal coronary vessel or a vessel of the brain, typically the guidewire has a diameter of 0.010–0.016 inch. This invention can also be applied to larger vessels which require larger diameter guidewires. Once a guidewire has been advanced along the vessel 164 and has reached the thrombotic deposit and lesion, guide catheter 32, the first tube, which serves as a flexible evacuation tube, can be advanced over the guidewire through tortuous turns to reach the thrombotic deposit and lesion. With the guide catheter distal end 33 of the guide catheter 32 positioned near the thrombotic deposit and lesion 166, the guidewire can then be removed from the guide catheter 32 and the patient's body. The jet cap 44 at the terminus of the second tube or hypo-tube 34 is then advanced within the lumen 87 of the guide catheter 32 until the transitional stop 40 contacts the stationary stop 150 of the guide catheter 32.

The arced surfaces 116a–116n at the extremities of the guide bars 112a–112n of the transitional stop 40 provide for guidance of the transitional stop 40 along the lumen 87 and also center the jet cap 44 in the center of the guide catheter 32 during initial transition and provide for centering of the jet cap 44 in the central bore 154 of the stationary stop 150 prior to engagement of the transitional stop 40 with the stationary stop 150. Engagement of the angled leading edges 114a–114n with the stationary stop 150 sets a predetermined gap or distance from the jet cap 44 proximal end to the stationary stop 150. The central bore 154 and lumen 87 of the guide catheter 32 serve as an evacuation tube at the guide catheter distal end 33. The rheolytic thrombectomy catheter 10 can then be activated by providing high pressure liquid, preferably saline, to the proximal end of the guide catheter 32 via the manifold 16.

High pressure saline, or other liquid, from the manifold 16 is provided and flows through the lumen 106 of the hypo-tube 34 to exit orifices 136 and 138 leading to the central cavity 140 of the jet cap 44. The high pressure saline exits jet orifices 128 and 130 as retrograde jets 170 of high velocity saline being directed toward the open central bore 154 in the stationary stop 150 at the guide catheter distal end 33. The high velocity saline jets 170 dislodge tissue from the thrombotic deposit and lesion 166 and entrain it into the saline jets 170 where it is broken up into smaller fragments. Impingement of the saline jets 170 onto the guide catheter distal end opening creates a stagnation pressure within the evacuation lumen 87 that drives the debris particles of tissue from the thrombotic deposit and lesion 166 toward the proximal end of the guide catheter 32.

A positive displacement piston PUMP (not illustrated) can be used to provide liquid, preferably saline, under pressure to the proximal end of the hypo-tube 34. A pressure ranging from 500–15,000 psi will provide the energy to create a useful high velocity jet as the saline exits the jet orifices 128 and 130 located at the circular end wall 120 of the jet cap 44. The flow rate of saline can be controlled by adjusting the pumping rate of the positive displacement pump. The proximal end of the guide catheter 32 interfaces with a suction device through the Luer connection 22 at the manifold branch 24, for example, a roller pump, prior to discharge of the evacuated thrombotic debris into a collection bag for disposal. The rate of evacuation can be controlled by adjusting the rate of the roller pump. The rate of saline inflow can be balanced with the rate of removal of thrombotic debris by simultaneous adjustment of the piston pump and the roller pump. The rate of saline inflow can be less than, equal to, or greater than the rate of removal of thrombotic debris. The rate of thrombus removal can be set to slightly exceed the rate of saline inflow to reduce the likelihood for distal embolization of thrombotic tissue.

Alternative Embodiments

Figure 15:
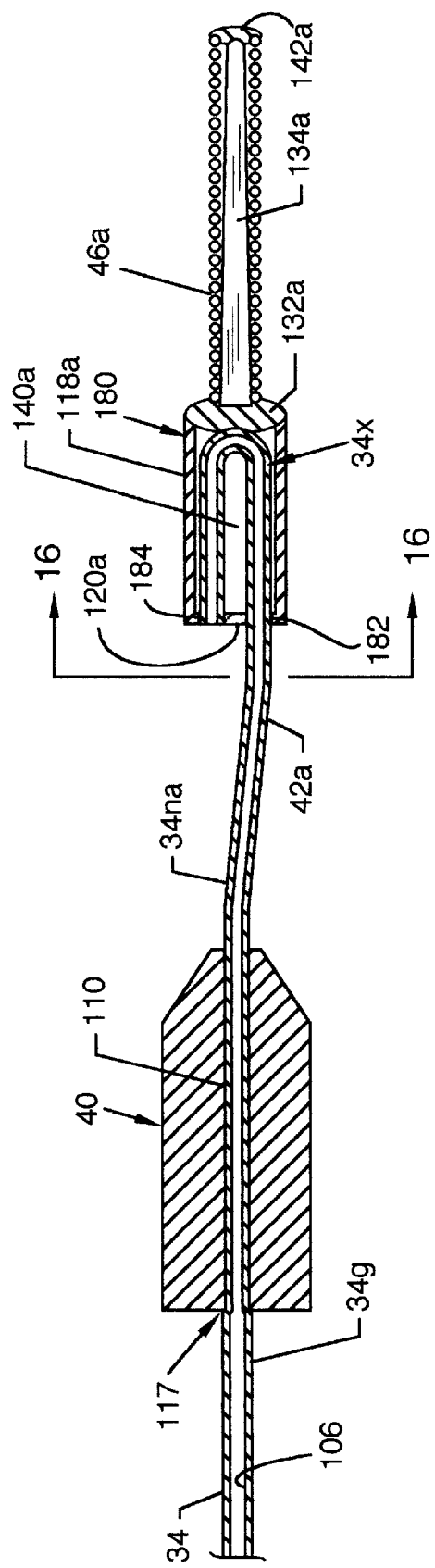
FIG. 15 is a longitudinal sectional view similar to FIG. 7 but illustrating an alternative jet cap embodiment.
Figure 16:
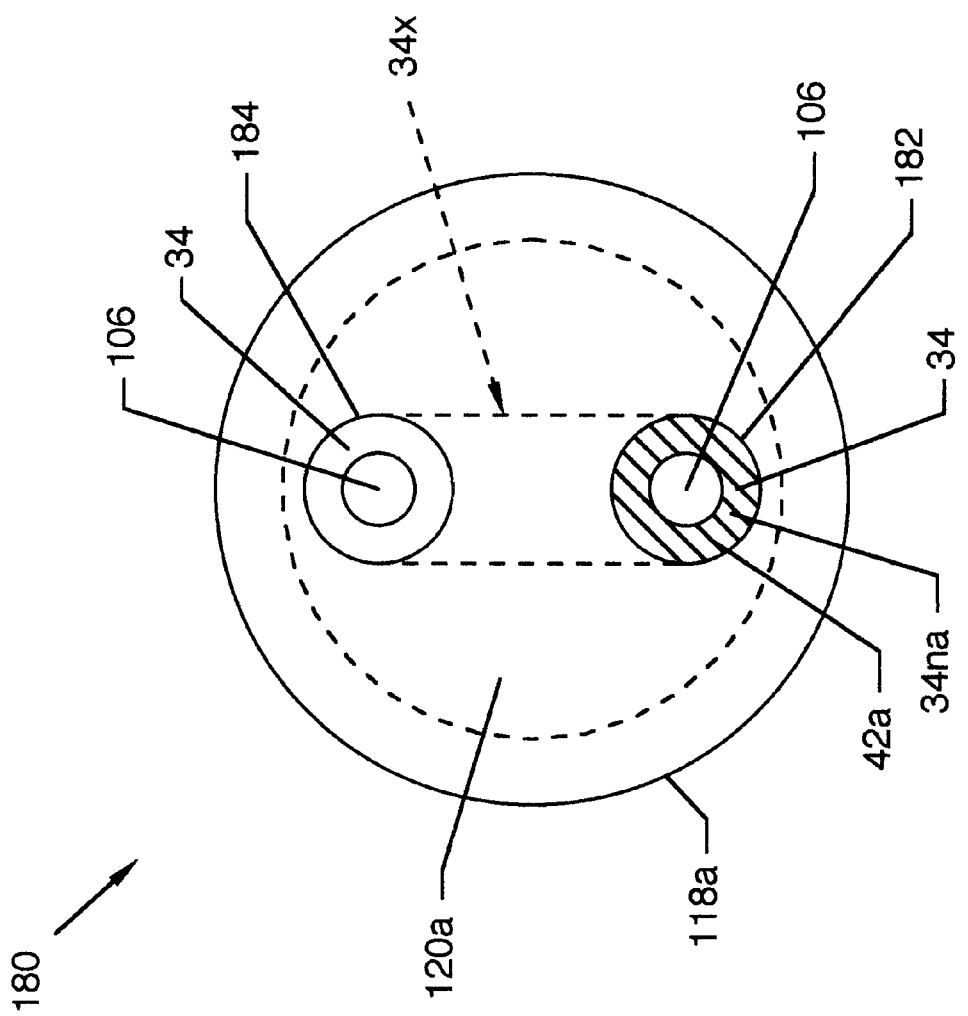
FIG. 16 is a view of the proximal end of the alternative jet cap embodiment shown in FIG. 15 looking in the direction of line 16—16 of FIG. 15, with the hypo-tube shown in cross section.

FIG. 15, a first alternative embodiment, illustrates a longitudinal sectional view of the transitional stop 40, an alternative jet cap 180, in lieu of jet cap 44, and a guidewire coil 46a aligned and secured over and about the hypo-tube 34 near or at a hypo-tube distal end 42a; and FIG. 16 illustrates a view of the jet cap 180 looking in the direction of line 16—16 of FIG. 15, where all numerals correspond to those elements previously described. The jet cap 180 includes several like components as described previously. The jet cap 180 aligns over and about and is secured to the last hypo-tube portion 34na, which angles downwardly from the longitudinal axis of the hypo-tube 34 at the hypo-tube distal end 42a. The jet cap 180 is tubular and includes a circular peripheral wall 118a and a circular end wall 120a extending inwardly from one end of the circular peripheral wall 118a. Located in the circular end wall 120a are two holes 182 and 184 which support a U-shaped hypo-tube portion 34x extending from the last hypo-tube portion 34na. The U-shaped hypo-tube portion 34x aligns to and extends through the holes 182 and 184 in the circular end wall 120a, as well as through the jet cap central cavity 140a. The free end portion of the U-shaped hypo-tube portion 34x secures in the hole 184 flush with the circular end wall 120a and is open, thereby defining an orifice aligned to direct a high velocity jet stream, preferably saline, in a proximal direction in a manner and fashion such as previously described. At the distal end of the circular peripheral wall 118a is a weld 132a which joins together the circular peripheral wall 118a, the bight of the U-shaped portion 34x of the hypo-tube 34, the guidewire coil 46a and a tapered core 134a. A weld 142a is also included at the distal end of the guidewire coil 46a to secure the end of the tapered core 134a to the guidewire coil 46a and to provide for smooth entry into a vessel or other body cavity.

FIG. 16 is a view of the proximal end of the first alternative jet cap embodiment looking in the direction of line 16—16 of FIG. 15, where all numerals correspond to those elements previously described.

Figure 17:
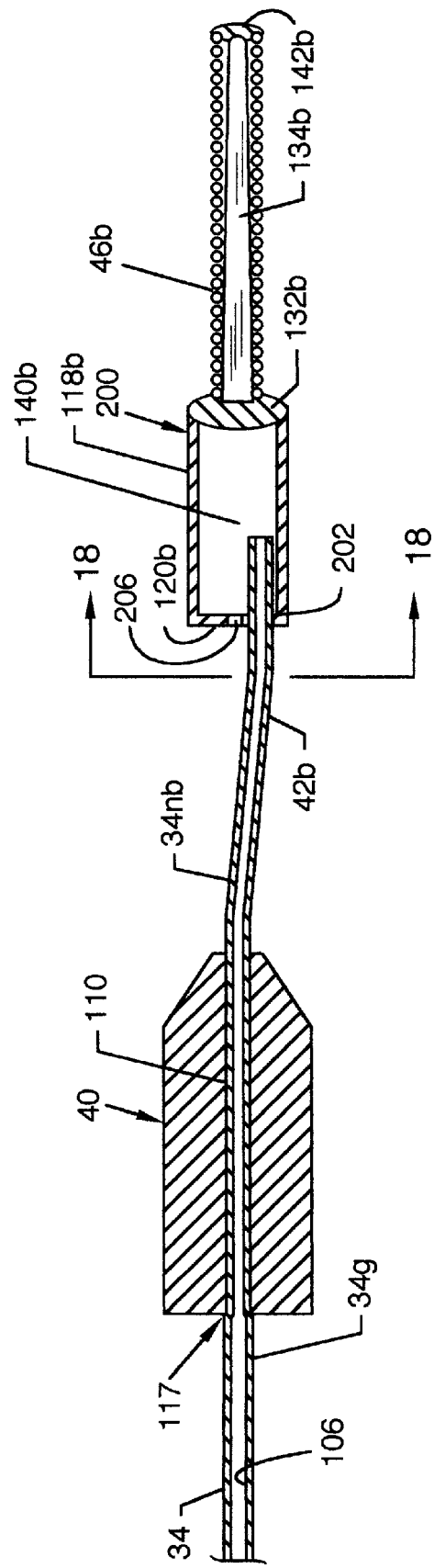
FIG. 17 is a longitudinal sectional view similar to FIG. 15 but illustrating another alternative jet cap embodiment.
Figure 18:
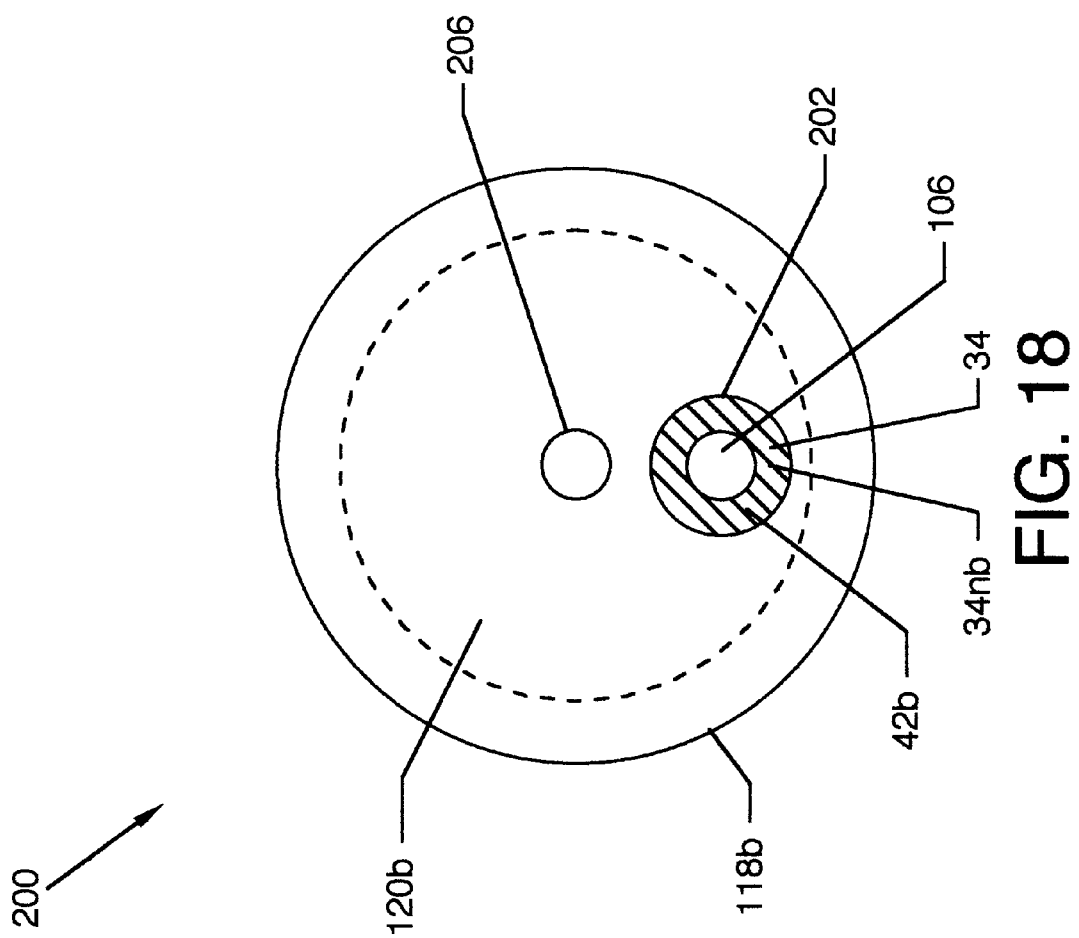
FIG. 18 is a view of the proximal end of the alternative jet cap embodiment shown in FIG. 17 looking in the direction of line 18—18 of FIG. 17, with the hypo-tube shown in cross section.

FIG. 17, a second alternative embodiment, illustrates a longitudinal sectional view of the transitional stop 40, an alternative jet cap 200, in lieu of jet cap 44, and a guidewire coil 46b aligned and secured over and about the hypo-tube 34 near or at a hypo-tube distal end 42b; and FIG. 18 illustrates a view of the jet cap 200 looking in the direction of line 18—18 of FIG. 17, where all numerals correspond to those elements previously described. The jet cap 200 includes several like components as described previously. The jet cap 200 aligns over and about and is secured to the last hypo-tube portion 34nb, which angles downwardly from the longitudinal axis of the hypo-tube 34 at the hypo-tube distal end 42b. The jet cap 200 is tubular and includes a circular peripheral wall 118b and a circular end wall 120b extending inwardly from one end of the circular peripheral wall 118b. Located in the circular end wall 120b is a hole 202, and, preferably, a centrally located jet orifice 206. Preferably one jet orifice is included, although more jet orifices can be utilized and shall not be deemed as limiting to the scope of the invention. The last hypo-tube portion 34nb aligns to and extends through the hole 202 in the circular end wall 120b and has an open end or orifice which ends in the jet cap central cavity 140b of the jet cap 200 for fluid communication from lumen 106 to the central cavity 140b and to the jet orifice 206 to direct a high velocity jet stream, preferably saline, in a proximal direction in a manner and fashion such as previously described. At the distal end of the circular peripheral wall 118b is a weld 132b which joins together the circular peripheral wall 118b, the guidewire coil 46b and a tapered core 134b. A weld 142b is also included at the distal end of the guidewire coil 46b to secure the end of the tapered core 134b to the guidewire coil 46b and to provide for smooth entry into a vessel or other body cavity.

FIG. 18 is a view of the proximal end of the second alternative jet cap embodiment looking in the direction of line 18—18 of FIG. 17, where all numerals correspond to those elements previously described.

Figure 19:
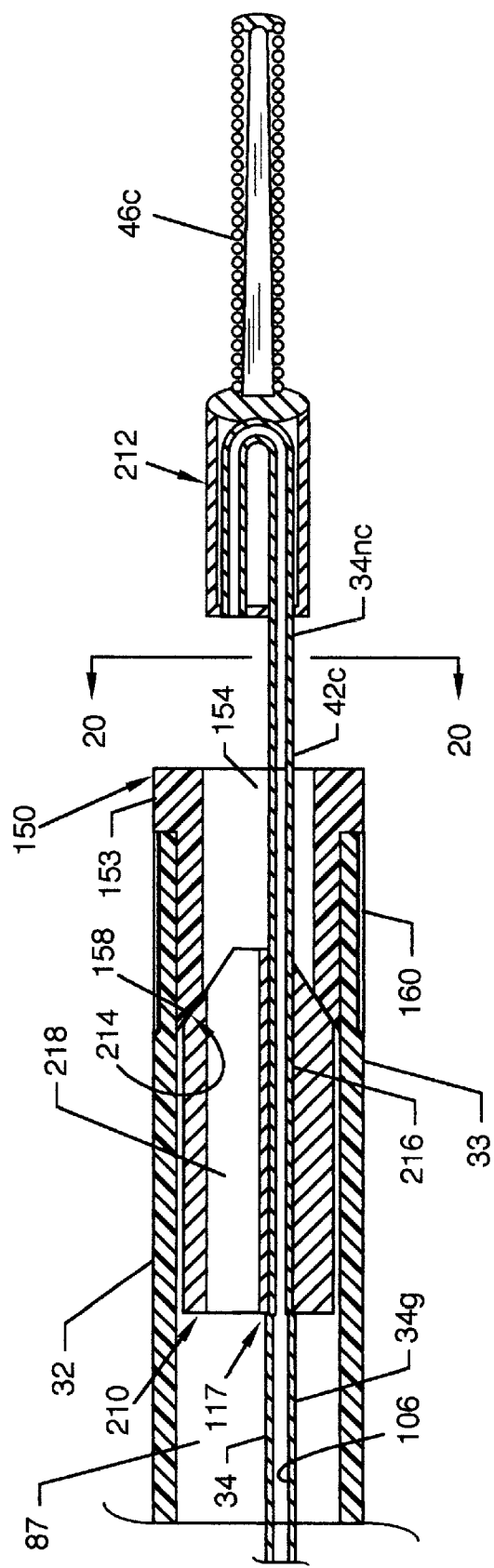
FIG. 19 is a longitudinal sectional view similar to FIG. 12 but illustrating an alternative transitional stop embodiment.
Figure 20:
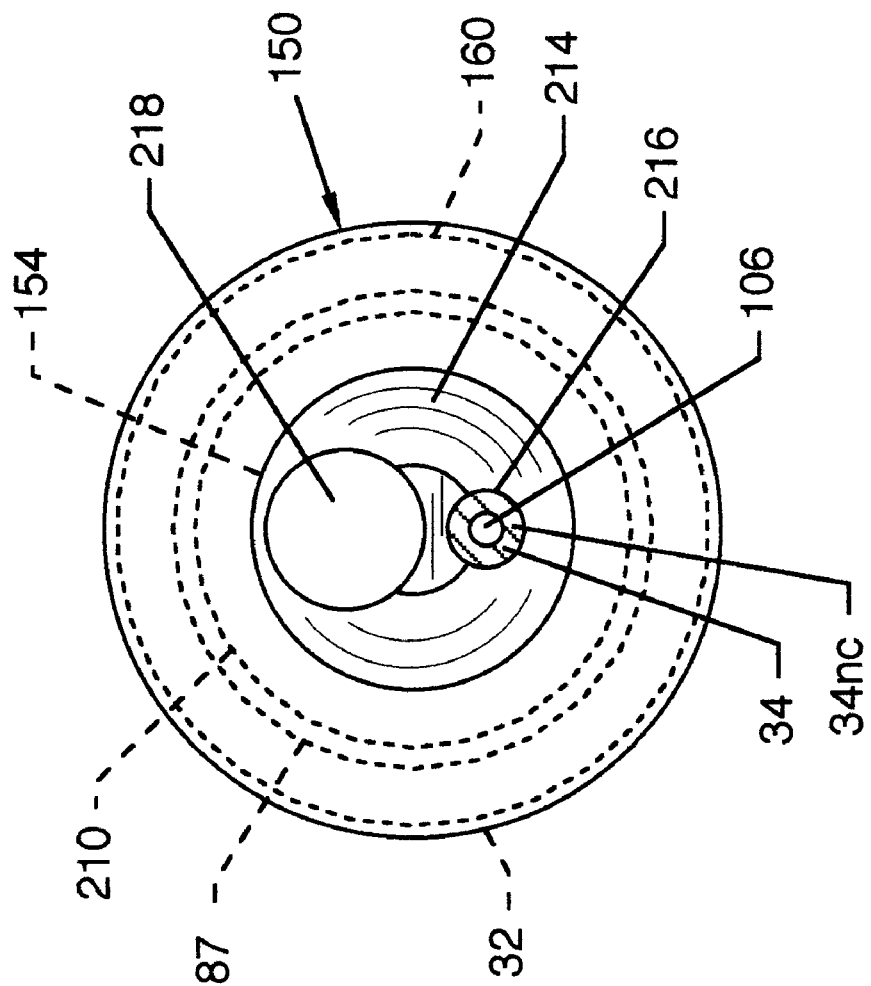
FIG. 20 is a view of the guide catheter distal end looking in the direction of line 20—20 of FIG. 19, with the hypo-tube shown in cross section.

FIG. 19, a third alternative embodiment, illustrates a longitudinal sectional view of a transitional stop 210, a jet cap 212 being similar to the configuration of jet cap 180 of FIG. 15 and in lieu of jet cap 44, and a guidewire coil 46c, being similar in configuration to guidewire coil 46a, aligned and secured over and about the hypo-tube 34 near or at a non-angled hypo-tube distal end 42c; and FIG. 20 illustrates a view of the guide catheter distal end 33 looking in the direction of line 20—20 of FIG. 19, where all numerals correspond to those elements previously described. In this embodiment the jet cap 212 aligns over and about and is secured to the last hypo-tube portion 34nc which projects straight outwardly from the lumen 87 and from transitional stop 210. The longitudinal axis of the hypo-tube 34 and the last hypo-tube portion 34nc is offset from the central axis of the transitional stop 210, at the hypo-tube distal end 42c. Having the last hypo-tube portion 34nc located off-center obviates the requirement of having a last hypo-tube portion which angles downwardly from the longitudinal axis of the hypo-tube 34 and also allows the jet cap 212 to align with the central bore 154 of the stationary stop 150 without having an angled last hypo-tube portion. The transitional stop 210 is fashioned of a solid material having a circular cross section, one end of which is in the form of a truncated cone having an angled annular surface 214 and also having a longitudinally oriented hole 216 distant from the central longitudinal axis of the transitional stop 210 and, in addition, a longitudinally oriented lumen 218 distant from the central longitudinal axis of the transitional stop 210. The transitional stop 210 is positioned as illustrated to position the angled annular surface 214 against the angled annular surface 158 of the stationary stop 150 to position the jet cap 212 at a desirable and finite distance from the stationary stop 150 at the guide catheter distal end 33 so that a high velocity jet stream, preferably saline, emanating from the open end or orifice of the hypo-tube may be directed in a proximal direction in a manner and fashion toward the lumen 218 to dislodge, break up and carry away thrombotic tissue debris, such as previously described.

FIG. 20 illustrates a view of the guide catheter distal end 33 looking in the direction of line 20—20 of FIG. 19, where all numerals correspond to those elements previously described.

Figure 21:
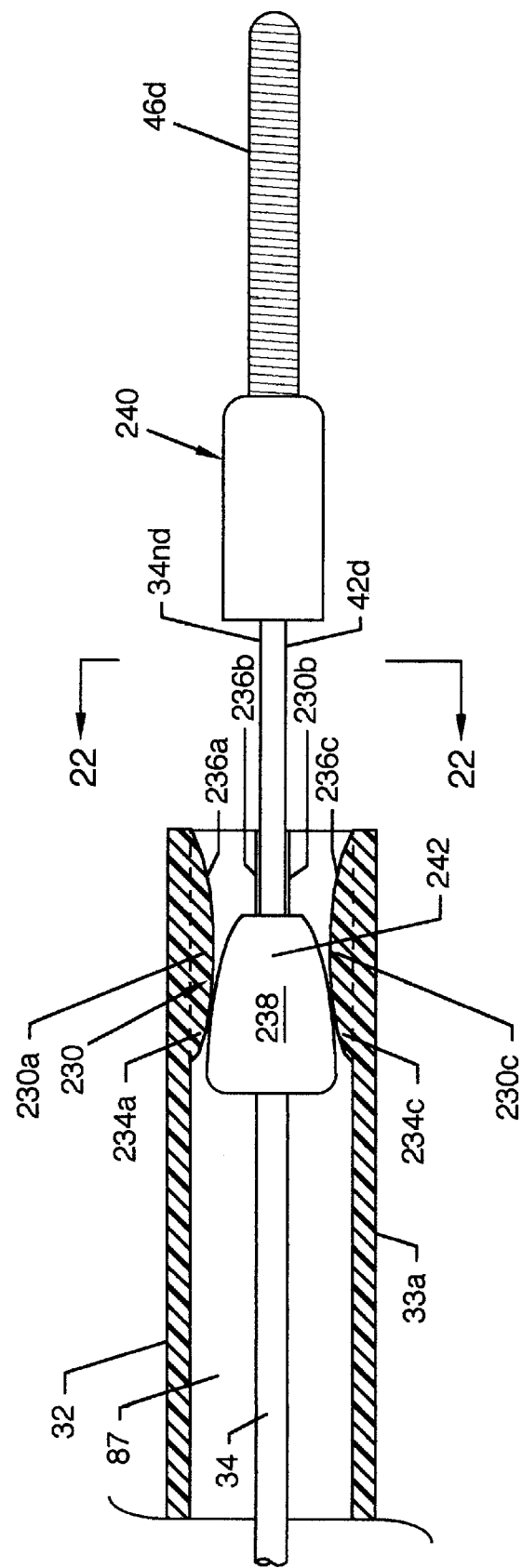
FIG. 21 is a view similar to FIG. 12 but illustrating alternative embodiments of the transitional stop and the stationary stop.

FIG. 21, a fourth alternative embodiment, illustrates a longitudinal sectional view of a guide catheter distal end 33a and having alternatively configured stationary and transitional stops, where all numerals correspond to those elements previously described. Located at the guide catheter distal end 33a of the guide catheter 32 is a stationary stop 230. The stationary stop 230 is permanently connected to, molded to, or otherwise formed to the tubing wall of the guide catheter 32 and projects into the lumen 87 of the guide catheter 32. By projecting inward and into the lumen 87, the stationary stop 230, being comprised of a plurality of arcuate stops 230a–230n, partially obstructs the lumen 87. However, the stationary stop 230 does not fully obstruct the lumen 87. Moreover, the stationary stop 230 allows for free passage of a standard guidewire through the lumen 87 in the region adjacent the guide catheter distal end 33a of the guide catheter 32. Preferably, and for purposes of example and illustration, the arrangement and dimensions of the stationary stop 230 are such that a coronary or neurological guidewire having a diameter of at least 0.010 inch, more preferably 0.016 inch, can freely pass the stationary stop 230. Most preferably, the unobstructed diameter of the stationary stop 230 is from about 0.010 inch to about 0.030 inch. The guide catheter 32 has an outer diameter of about 0.040 inch and an inner diameter of about 0.028 inch or about 4 French or smaller. As is well known in the art, the guide catheter 32 may be advanced and maneuvered through the vasculature such that the guide catheter distal end 33a may be selectively positioned adjacent to the site of desired surgical action, for example, adjacent to a thrombus obstructing a blood vessel.

The stationary stop 230 has a plurality of arcuate stops 230a–230n aligned parallel to the central axis of the guide catheter 32, each having a proximal tapered surface 234a–234n and a distal tapered surface 236a–236n. The stationary stop 230 may be formed from a variety of materials. Preferably, the stationary stop 230 is formed of material identical to that of the guide catheter 32. Most preferably, the stationary stop 230 is fabricated by a permanent deformation and thickening of the wall of the guide catheter 32 at the desired location. Alternatively, the stationary stop 230 might be separately constructed and then fixed within the guide catheter 32.

The hypo-tube 34, or second tube, is fashioned as previously described having a hypo-tube distal end 42d and a proximal end (not shown). A transitional stop 238 is mounted on the last hypo-tube portion 34nd at a location spaced apart from a jet cap 240 and a guidewire coil 46d also mounted on the last hypo-tube portion 34nd. The transitional stop 238 has a cross sectional extent such that it may not freely pass the stationary stop 230. In one embodiment, the transitional stop 238 has a rounded cross section when viewed axially. However, numerous alternative shapes might be employed for the transitional stop 238 provided that at least passage past the stationary stop 230 is prevented. Preferably, the distal surface 242 of the transitional stop 238 is tapered, such that a distalmost extent of the transitional stop 238 presents a cross section capable of passing the proximalmost extent of the stationary stop 230, generally as represented by the proximal tapered surfaces 234a–234n. Distal tapered surface 242 serves a dual function by first facilitating passage and advancement of the hypo-tube 34 by reducing any tendency to catch or bind within the guide catheter 32, and second, to desirably laterally position the transitional stop 238 relative to the stationary stop 230 and thereby generate lateral relations, such as for example, a concentric relationship between the guide catheter 32 and hypo-tube 34, respectively. Preferably, the cross sectional extent of the transitional stop 238 is roughly about 0.010 inch to about 0.030 inch; however, the critical consideration in cross sectional dimensions of the transitional stop 238 is that it must pass through the lumen 87 of the guide catheter 32 and yet not pass the stationary stop 230.

As previously mentioned, a jet cap 240 is mounted at the hypo-tube distal end 42d of the hypo-tube 34. A guidewire coil 46d extends distally from the jet cap 240. The jet cap 240, guidewire coil 46 and transitional stop 238 are radially symmetrical about the longitudinal extent of the hypo-tube 34. The jet cap 240 preferably has a diameter of from about 0.010 inch to about 0.030 inch. The hypo-tube 34 preferably has an outer diameter of about 0.008 inch to about 0.018 inch and also includes a continuous high pressure lumen 106 extending from the proximal end to the hypo-tube distal end 42d and continuing into the jet cap 240. When the end of the hypo-tube 34 is advanced through the lumen 87 of the guide catheter 32, the guidewire coil 46d adjacent the jet cap 240 and any portion of the hypo-tube 34 distal from the transitional stop 238 are free to pass the location of the stationary stop 230. However, passage of the transitional stop 238 is prevented by the partial obstruction of the lumen 87 of guide catheter 32 by the stationary stop 230. Thus, when the distal tapered surface 242 of the transitional stop 238 engages the proximal tapered surfaces 234a–234n of the stationary stop 230, a desired longitudinal relationship is dependably generated between the jet cap 240 and the guide catheter distal end 33a. Most importantly, the jet cap 240 is oriented and spaced apart and distally situated at a desired relationship to the distal end 33a of the guide catheter 32.

Figure 22:
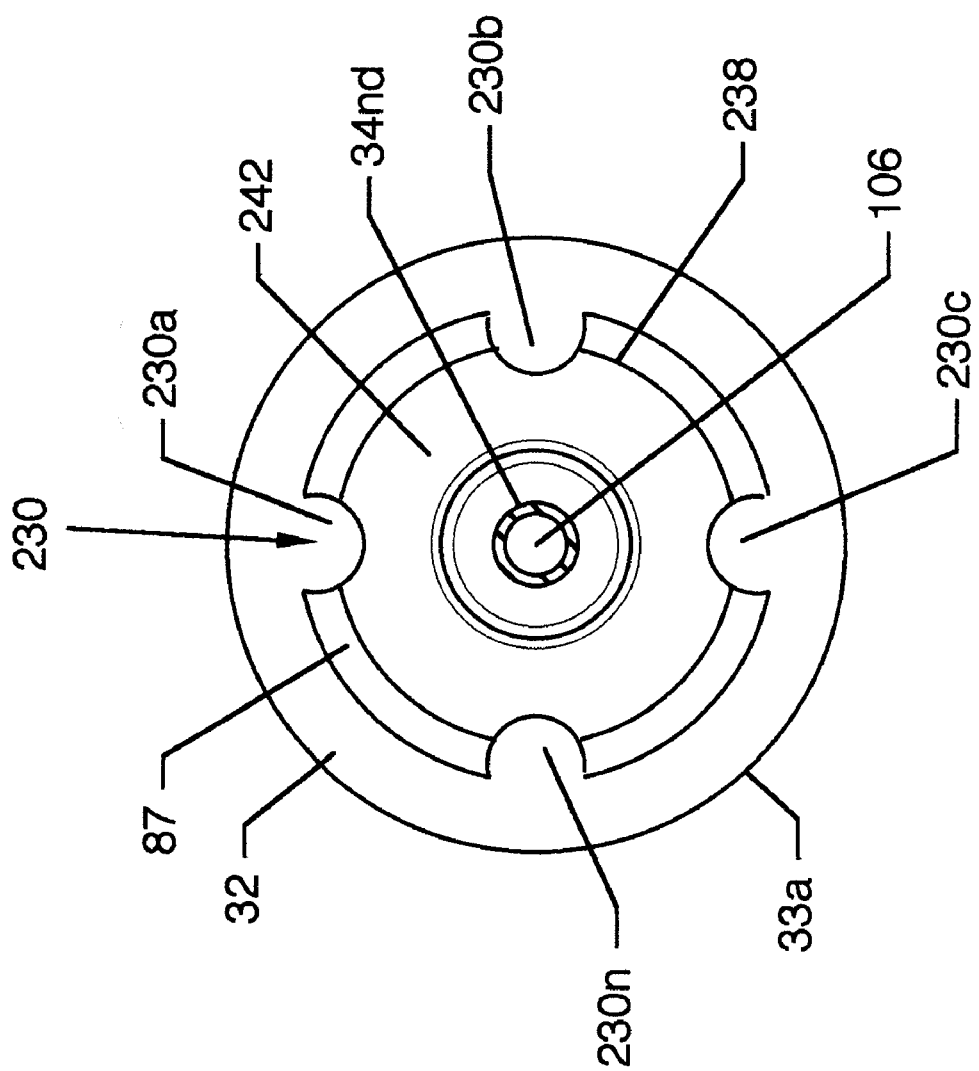
FIG. 22 is a view of the guide catheter distal end looking in the direction of line 22—22 of FIG. 21, with the hypo-tube shown in cross section; and, FIG. 23 is a side view in partial cross section of a fifth alternative embodiment of the guide catheter distal end, where the hypo-tube is fixed along the longitudinal axis of the guide catheter.

FIG. 22 illustrates a view of the guide catheter distal end 33a looking in the direction of line 22—22 of FIG. 21, where all numerals correspond to those elements previously described. Illustrated in particular are the plurality of arcuate stops 230a–230n shown in contact with the distal tapered surface 242 of the transitional stop 238. Fluids containing thrombotic debris can pass between the arcuate stops 230a–230n, along the inner wall of the guide catheter 32 which is adjacent to and between the arcuate stops 230a–230n, along the transitional stop 238, and into the lumen 87 of the guide catheter 32 for passage to the manifold 16.

Figure 23:
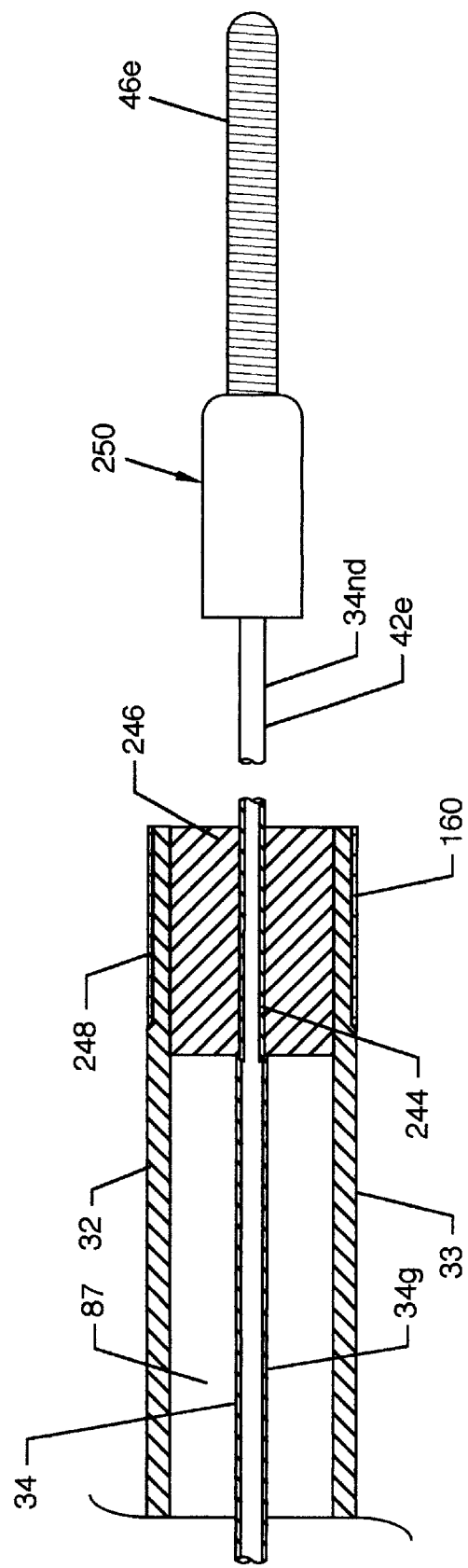

FIG. 23, a fifth alternative embodiment, illustrates, in partial cross section, a side view of the guide catheter distal end 33 where the hypo-tube 34 is fixed along the longitudinal axis of the guide catheter 32, where all numerals correspond to those elements previously described. In this embodiment of a one-piece catheter, the hypo-tube 34 is appropriately aligned and secured in a central bore 244 of a cylindrical fixture 246 which secures in the end of the guide catheter 32 by a crimp sleeve 248. A jet cap 250 and a guidewire coil 46e secure to the hypo-tube distal end 42e at the last hypo-tube portion 34ne at a fixed distance from the guide catheter distal end 33. In this embodiment, no transitional or stationary stops are incorporated, as the entire catheter system incorporating a longitudinally fixed hypo-tube 34 is inserted into the body without use of a guidewire. The cylindrical fixture 246 has passages with the same profile as passages 162a–162n of the transitional stop 40 for connection to lumen 87 in the guide catheter 32.

Because numerous modifications may be made to this invention without departing from the spirit thereof, the scope of the invention is not to be limited to the embodiments illustrated and described. Rather, the scope of the invention is to be determined by the appended claims and their equivalents. The tip can be radio-opaque. The guidewire can be a braided polymer or other suitable material.

While each of the the parts 44, 180, 200, 212, 240, and 250 representing means positioned at the distal end of the high pressure tube and coacting with the distal end of the high pressure tube for directing fluid toward the open end of the evacuation tube has been characterized throughout the description as a "jet cap", it is here pointed out that this term "jet cap" is not of common usage in the art but, rather, has been introduced as a convenient expression by which to indicate the general character of these parts, in that they act in the nature of a cap at the distal end of the high pressure tube and serve in coaction with the distal end of the high pressure tube to direct one or more jets of fluid proximally toward the open distal end of the evacuation tube. Accordingly, the term "jet cap" is not to be construed in a limiting sense as defining a particular structure, but is to be regarded as merely signifying the general nature of the instrumentally provided for directing fluid in the manner described.

While each of the parts 44, 180, 200, 212, 240 and 250 representing means positioned at the distal end of the high pressure tube and coacting with the distal end of the high pressure tube for directing fluid toward the open end of the evacuation tube has been characterized thoughout the description as a "jet cap", it is here pointed out that this term "jet cap" is not of common usage in the art but, rather, has been introduced as a convenient expression by which to indicate the general character of these parts, in that they act in the nature of a cap at the distal end of the high pressure tube and serve in coaction with the distal end of the high pressure tube to direct one or more jets of fluid proximally toward the open distal end of the evacuation tube. Accordingly, the term "jet cap" is not to be construed in a limiting sense as defining a particular structure, but is to be regarded as merely signifying the general nature of the instrumentally provided for directing fluid in the manner described.

It is claimed:

1. A catheter for removing material from a body cavity comprising:
    a. an outer assembly including
        (1) a first tube having a lumen with an open distal end and an internally located stationary stop partially obstructing said lumen at said open distal end and,
    b. an inner assembly including
        (1) a second tube insertable into said first tube, said second tube having a high pressure lumen having a distal end, said distal end having an orifice;
        (2) a transitional stop fixed to said second tube adjacent to said distal end; and,
        (3) means positioned at said distal end of said second tube and coacting with said distal end of said second tube for directing fluid exiting said orifice toward said open distal end of said first tube, said second tube being movable axially within said first tube such that said transitional stop engages said stationary stop to hold said means in a desired relationship with respect to said open distal end of said first tube.

2. A catheter for removing material from a body vessel or other body cavity comprising:
    a. an outer assembly including
        (1) an evacuation tube having a proximal end and an open distal end containing a stationary stop and having an evacuation lumen; and,
    b. an inner assembly including
        (1) a high pressure tube having a high pressure lumen, said high pressure tube having a proximal end and a distal end, said distal end having one or more orifices through which fluid can exit from said high pressure lumen to be directed toward said open distal end of said evacuation tube;
        (2) a transitional stop fixed to said high pressure tube at a position closer to said distal end than to said proximal end; and,
        (3) means positioned at said distal end of said high pressure tube and coacting with said distal end of said high pressure tube to direct fluid toward said open distal end of said evacuation tube.

3. The catheter of claim 2, wherein said means has a distal end and said distal end of said jet cap has a guidewire coil attached thereto to assist in advancement of said outer assembly and said inner assembly together or separately within the body vessel or other body cavity.

4. The catheter of claim 2, wherein said means is configured to create a jet of fluid and to direct it toward said open distal end of said evacuation tube.

5. The catheter of claim 2, wherein said evacuation tube is flexible and can pass over a guidewire through tortuous pathways.

6. A method of removing material from a body vessel or other body cavity comprising the steps of:

a. providing a guidewire and a first catheter having an open distal end and an internally located stationary stop positioned adjacent to the open distal end;

b. advancing the guidewire to a body cavity site containing material to be removed;

c. advancing the first catheter over the guidewire to the body cavity site containing material to be removed to position the distal end at the body cavity site;

d. removing the guidewire from the first catheter;

e. providing a second catheter carrying a means for directing fluid and a transitional stop spaced apart from the means for directing fluid;

f. advancing the second catheter within the first catheter to engage the transitional stop with the stationary stop; and, g. providing a high pressure fluid supply to the second catheter so as to cause fluid to emanate therefrom and to impinge upon and dislodge the material to be removed and force it into the open distal end of the first catheter.

7. The method of claim 6, wherein the means for directing fluid carries a distally projecting coil to facilitate further distal advancement of the first catheter and the second catheter together or separately within the body vessel or other body cavity to a further body cavity site containing material to be removed so as to remove additional distally situated material.

8. A catheter combination comprising:

a. a first tube having an open distal end and a lumen extending to the open distal end;

b. a second tube, separable from the first tube, and insertable within the lumen of the first tube, the second tube having a distal end and a lumen extending to the distal end;

c. means connected to the second tube at the distal end of the second tube and coacting with the distal end of the second tube for directing fluid exiting the lumen of the second tube, toward the open distal end of the first tube, said means being capable of passage through the lumen of the first tube and being characterized by the ability to provide a localized region of low pressure associated with a liquid flow directed generally proximally and into the lumen of the first tube through the open distal end of the first tube when located and oriented appropriately relative to the open distal end of the first tube; and, d. means for indexing an appropriate positional relationship of said means and the distal end of the second tube relative to the open distal end of the first tube, the means for indexing comprising a transitional stop fixed to the second tube adjacent to the distal end of the second tube.

RHEOLYTIC THROMBECTOMY CATHETER AND
METHOD OF USING SAME
PARTS LIST

| | |
|---|---|
| 10 | rheolytic thrombectomy catheter |
| 12 | outer assembly |
| 14 | inner assembly |
| 16 | manifold |
| 18 | hemostasis nut |
| 20 | manifold proximal end |
| 22 | Luer connection |

-continued

RHEOLYTIC THROMBECTOMY CATHETER AND
METHOD OF USING SAME
PARTS LIST

| | |
|---|---|
| 23 | proximal end (branch) |
| 24 | branch |
| 26 | Luer fitting |
| 28 | distal manifold end |
| 30 | strain relief |
| 31 | tube |
| 32 | first tube or guide catheter |
| 33 | guide catheter distal end |
| 33a | guide catheter distal end |
| 34 | second tube or hypo-tube |
| 34a–n | hypo-tube portions |
| 34n | last hypo-tube portion |
| 34na | last hypo-tube portion |
| 34ne | last hypo-tube portion |
| 34nc | last hypo-tube portion |
| 34nd | last hypo-tube portion |
| 34x | U-shaped hypo-tube portion |
| 36 | filter housing/high pressure connection assembly |
| 38 | hypo-tube proximal end |
| 40 | transitional stop |
| 42 | hypo-tube distal end |
| 42a | hypo-tube distal end |
| 42b | hypo-tube distal end |
| 42c | hypo-tube distal end |
| 42d | hypo-tube distal end |
| 42e | hypo-tube distal end |
| 44 | jet cap |
| 46 | quidewire coil |
| 46a | guidewire coil |
| 46b | guidewire coil |
| 46c | guidewire coil |
| 46d | guidewire coil |
| 46e | guidewire coil |
| 48 | central passage |
| 50 | branch passage |
| 52 | multi-radius cavity |
| 54 | round outer cavity portion |
| 56 | round inner cavity portion |
| 58 | threaded surface |
| 60 | seal |
| 61 | distal annular surface |
| 62 | body |
| 63 | annular surface |
| 64 | grasping surface |
| 66 | threaded surface |
| 68 | passageway |
| 72 | filter |
| 74 | central bore |
| 76 | annular flange |
| 78 | tapered proximal tube mouth end |
| 80 | distal tube end |
| 82 | tapered tube surface |
| 84 | threads |
| 86 | threads |
| 87 | lumen (of 32) |
| 88 | tapered central passage surface |
| 90 | body |
| 92 | threaded surface |
| 94 | tubular cavity |
| 96 | fine filter |
| 98 | course filter |
| 100 | central passage |
| 102 | cap |
| 104 | central bore |

RHEOLYTIC THROMBECTOMY CATHETER AND METHOD OF USING SAME
PARTS LIST -continued

| Number | Description |
|---|---|
| 106 | lumen (of 34) |
| 108 | body |
| 110 | central bore |
| 112a–n | guide bars |
| 114a–n | angled leading edges |
| 116a–n | arced surfaces |
| 117 | shoulder-like transition |
| 118 | peripheral wall |
| 118a | peripheral wall |
| 118b | peripheral wall |
| 120 | circular end wall |
| 120a | circular end wall |
| 120b | circular end wall |
| 122 | elongated hole |
| 124 | arcuate portion |
| 126 | arcuate portion |
| 128 | jet orifice |
| 130 | jet orifice |
| 132 | weld |
| 132a | weld |
| 132b | weld |
| 134 | tapered core |
| 134a | tapered core |
| 136 | orifice |
| 138 | orifice |
| 140 | central cavity |
| 140a | central cavity |
| 140b | central cavity |
| 142 | weld |
| 142a | weld |
| 142b | weld |
| 144 | jet orifice |
| 146 | jet orifice |
| 148 | bore |
| 150 | stationary stop |
| 152 | cylindrical body |
| 153 | cap |
| 154 | central bore |
| 156 | shoulder |
| 158 | angled annular surface |
| 160 | crimp sleeve |
| 162a–n | passages |
| 164 | blood vessel |
| 166 | thrombotic deposit and lesion |
| 170 | saline jet |
| 180 | jet cap |
| 182 | hole |
| 184 | hole |
| 200 | jet cap |
| 202 | hole |
| 206 | jet orifice |
| 210 | transitional stop |
| 212 | jet cap |
| 214 | angled annular surface |
| 216 | hole |
| 218 | lumen |
| 230 | stationary stop |
| 230a–n | arcuate stops |
| 234a–n | proximal tapered surfaces |
| 236a–n | distal tapered surfaces |
| 238 | transitional stop |
| 240 | jet cap |
| 242 | distal tapered surface |
| 244 | central bore |
| 246 | cylindrical fixture |
| 248 | crimp sleeve |
| 250 | jet cap |

* * * * *